US012064198B2

(12) United States Patent
Dunki-Jacobs

(10) Patent No.: US 12,064,198 B2
(45) Date of Patent: Aug. 20, 2024

(54) SURGICAL INSTRUMENTS FOR ROBOTIC-ASSISTED SURGERY AND METHODS OF USING THE SAME

(71) Applicant: Standard Bariatrics, Inc., Cincinnati, OH (US)

(72) Inventor: Adam Robert Dunki-Jacobs, Cincinnati, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

(21) Appl. No.: 18/199,558

(22) Filed: May 19, 2023

(65) Prior Publication Data

US 2023/0372035 A1 Nov. 23, 2023

Related U.S. Application Data

(60) Provisional application No. 63/344,210, filed on May 20, 2022.

(51) Int. Cl.
*A61B 34/30* (2016.01)
*A61B 17/072* (2006.01)
(Continued)

(52) U.S. Cl.
CPC .......... *A61B 34/30* (2016.02); *A61B 17/3423* (2013.01); *A61F 5/0083* (2013.01);
(Continued)

(58) Field of Classification Search
CPC .............. A61B 2034/302; A61B 34/30; A61B 17/3423; A61B 17/068; A61B 17/0684;
(Continued)

(56) References Cited

U.S. PATENT DOCUMENTS

2007/0089557 A1    4/2007  Solomon et al.
2009/0024142 A1*   1/2009  Ruiz Morales ........ A61B 34/37
                                                   606/130
(Continued)

OTHER PUBLICATIONS

International Search Report and Written Opinion of the International Searching Authority received in International Patent App. No. PCT/US2023/022888; mailed Oct. 10, 2023; 10 pages.

*Primary Examiner* — Stephen F. Gerrity
*Assistant Examiner* — Linda J Hodge

(57) ABSTRACT

A surgical system and device for use with a computerized surgical manipulation system, wherein the computerized surgical manipulation system includes a robotic arm and a support coupled to the robotic arm for receiving various instruments, comprising a surgical device, wherein the surgical device includes an elongated shaft; and a control housing coupled to the elongated shaft, wherein the control housing is configured to attach to a motor housing having a notch, wherein the motor housing is coupled to the support; and a trocar pivotally coupled to the support such that the trocar can pivot away from axial alignment with the support, wherein the elongated shaft extends into the pivoted trocar, wherein the trocar containing the surgical device is pivoted into axial alignment with the support such that the notch receives the elongated shaft of the surgical device, and wherein the control housing engages the motor housing.

15 Claims, 26 Drawing Sheets

(51) Int. Cl.
*A61B 17/34* (2006.01)
*A61F 5/00* (2006.01)

(52) U.S. Cl.
CPC ............... *A61B 2017/07257* (2013.01); *A61B 2017/07271* (2013.01); *A61B 2034/302* (2016.02)

(58) Field of Classification Search
CPC .............. A61B 17/0686; A61B 17/072; A61B 17/07207; A61B 2017/07257; A61B 2017/07271; A61B 2017/07285; A61B 2017/00477; A61F 5/0083
USPC ............................................ 227/175.1–182.1
See application file for complete search history.

(56) References Cited

U.S. PATENT DOCUMENTS

| | | |
|---|---|---|
| 2016/0000512 A1 | 1/2016 | Gombert et al. |
| 2017/0348063 A1* | 12/2017 | Braun .................... A61B 34/30 |
| 2018/0049824 A1 | 2/2018 | Harris et al. |
| 2018/0168689 A1* | 6/2018 | Beckman ............... A61B 90/50 |
| 2019/0046193 A1 | 2/2019 | Dunki-Jacobs et al. |
| 2020/0000532 A1* | 1/2020 | Kreissig ................. A61B 34/30 |
| 2021/0052343 A1 | 2/2021 | Overmyer |
| 2021/0113241 A1 | 4/2021 | Forster et al. |
| 2022/0031315 A1* | 2/2022 | Bakos ................... A61B 17/068 |
| 2022/0079588 A1* | 3/2022 | Harris ................... A61B 17/072 |
| 2023/0035946 A1* | 2/2023 | Kapadia ................. A61B 34/37 |

\* cited by examiner

SURGICAL INSTRUMENTS FOR ROBOTIC-ASSISTED SURGERY AND METHODS OF USING THE SAME

CROSS-REFERENCE TO RELATED APPLICATIONS

This patent application claims the benefit of U.S. Provisional Patent Application Ser. No. 63/344,210 filed on May 20, 2022 and entitled "Surgical Instruments For Robotic-Assisted Surgery and Methods of Using the Same", the disclosure of which is hereby incorporated by reference herein in its entirety and made part of the present U.S. utility patent application for all purposes.

BACKGROUND

The disclosed technology relates in general to robotic-assisted surgical technology and more specifically to end effectors and stapling devices and methods of using those devices in robotic-assisted surgical procedures.

Robotic surgery, also called robot-assisted surgery, allows doctors to perform many types of complex procedures with more precision, flexibility, and control than is possible with conventional techniques. Robotic surgery is usually associated with minimally invasive surgery, i.e., procedures performed through small incisions. It is also sometimes used in certain traditional open surgical procedures.

Example clinical robotic surgical system can include a camera arm and mechanical arms with supports for attaching surgical instruments. The doctors control the arms while seated at a computer console near the operating table. The console gives the doctors a high-definition, magnified, 3D view of the surgical site.

Minimally invasive surgical devices in the prior art are generally long (e.g., 35 mm to 60 mm) and thin (e.g., 5 mm to 15 mm diameter). Because the spatial environment in minimally invasive surgery is limited, conventional surgical devices may be too long or thin for use with certain robotic surgical systems. Further, these conventional surgical devices can present mechanical issues because of their long and thin design. B-shaped staple formation typically requires a pressure between 5-25 g/mm$^2$, with a target pressure of 15 g/mm$^2$. Thus, such conventional surgical stapling devices used with robotic surgical systems often form small, less rigid staples under smaller pressures because of their long and thin design. Accordingly, there is an ongoing need for a surgical device and system that is adapted for use with existing computerized surgical manipulation systems such that the surgical device maintains its mechanical function.

SUMMARY

The following provides a summary of certain example implementations of the disclosed technology. This summary is not an extensive overview and is not intended to identify key or critical aspects or elements of the disclosed technology or to delineate its scope. However, it is to be understood that the use of indefinite articles in the language used to describe and claim the disclosed technology is not intended in any way to limit the described technology. Rather the use of "a" or "an" should be interpreted to mean "at least one" or "one or more".

One implementation of the disclosed technology provides a surgical system for use with a computerized surgical manipulation system, wherein the computerized surgical manipulation system includes a robotic arm and a support coupled to the robotic arm for receiving various instruments, comprising a surgical device, wherein the surgical device includes an elongated shaft having a proximal end and a distal end; and a control housing coupled to the proximal end of the elongated shaft, wherein the control housing is configured to attach to a motor housing having a notch formed therein, wherein the motor housing is coupled to the support; and a trocar pivotally coupled to the support such that the trocar can pivot away from axial alignment with the support, wherein the distal end of the elongated shaft extends into the pivoted trocar, wherein the trocar containing the surgical device is pivoted into axial alignment with the support such that the notch receives the elongated shaft of the surgical device, and wherein the control housing engages the motor housing.

The surgical device may further include an end effector coupled to the distal end of the elongated shaft, wherein the end effector includes a clamping mechanism having an anvil and a cartridge for containing surgical staples. The system may further comprise a closure mechanism for opening and closing the anvil on the clamping mechanism, wherein the closure mechanism is housed within the elongated shaft of the surgical device; and a firing mechanism for activating the cartridge, wherein the firing mechanism includes a laminate beam having a proximate end and a distal end, wherein a blade is coupled to the distal end of the laminate beam, and wherein the proximate end of the laminate beam is located in diversion channels within the elongated shaft of the surgical device; and a nut affixed to a rotating member, wherein the nut is coupled to the proximate end of the laminate beam wherein the firing system moves the nut from the distal end of the surgical device towards the proximal end of the surgical device, and wherein the laminate beam delaminates as it moves through the diversional channels. The trocar may include a holding feature having an inner wall and an outer wall. The holding feature of the trocar is pivotally coupled to the support through a gripping member, wherein an angled gap is formed between the gripping member and the inner wall when the trocar is axially aligned with the support, and wherein a second angled gap is formed between the gripping member and the outer wall when the trocar is pivoted away from axial alignment with the support. The elongated shaft has a diameter portion and a reduced diameter portion, wherein the reduced diameter portion engages the notch on the motor housing. The control housing has a control interface, wherein the motor housing has a motor interface, and wherein the control interface selectively attaches to the motor interface to join the control housing and the motor housing. The control interface and the motor interface each include a plurality of platters that are associated with specific mechanical features of the surgical device, wherein the platters on the control interface are configured to mate with the platters on the motor interface. The system may further comprise a bailout mechanism configured to the control housing for manually controlling mechanical operations of the surgical device.

Another implementation of the disclosed technology provides a surgical system for use with a computerized surgical manipulation system, wherein the computerized surgical manipulation system includes a robotic arm and a support coupled to the robotic arm for receiving various instruments, comprising a surgical device, wherein the surgical device includes an elongated shaft having a proximal end and a distal end; and a control housing coupled to the proximal end of the elongated shaft, wherein the control housing is configured to attach to a motor housing having a notch formed therein, wherein the motor housing is coupled to the support; and a trocar having a holding feature, wherein the holding feature has an inner wall and an outer wall, wherein the holding feature is pivotally coupled to the support such that the trocar can pivot away from axial alignment with the support, wherein the distal end of the elongated shaft extends into the pivoted trocar, wherein the trocar containing the surgical device is pivoted into axial alignment with the support such that the notch receives the elongated shaft of the surgical device, and wherein the control housing engages the motor housing.

The surgical device may further include an end effector coupled to the distal end of the elongated shaft, wherein the end effector includes a clamping mechanism having an anvil and a cartridge for containing surgical staples. The system may further comprise a closure mechanism for opening and closing the anvil on the clamping mechanism, wherein the closure mechanism is housed within the elongated shaft of the surgical device; and a firing mechanism for activating the cartridge, wherein the firing mechanism includes a laminate beam having a proximate end and a distal end, wherein a blade is coupled to the distal end of the laminate beam, and wherein the proximate end of the laminate beam is located in diversion channels within the elongated shaft of the surgical device; and a nut affixed to a rotating member, wherein the nut is coupled to the proximate end of the laminate beam, wherein the firing system moves the nut from the distal end of the surgical device towards the proximal end of the surgical device, and wherein the laminate beam delaminates as it moves through the diversional channels. The holding feature of the trocar is pivotally coupled to the support through a gripping member, wherein an angled gap is formed between the gripping member and the inner wall when the trocar is axially aligned with the support, and wherein a second angled gap is formed between the gripping member and the outer wall when the trocar is pivoted away from axial alignment with the support. The elongated shaft has a diameter portion and a reduced diameter portion, wherein the reduced diameter portion engages the notch on the motor housing. The control housing has a control interface, wherein the motor housing has a motor interface, and wherein the control interface selectively attaches to the motor interface to join the control housing and the motor housing. The control interface and the motor interface each include a plurality of platters that are associated with specific mechanical features of the surgical device, wherein the platters on the control interface are configured to mate with the platters on the motor interface. The system may further comprise a bailout mechanism configured to the control housing for manually controlling mechanical operations of the surgical device.

Still another implementation of the disclosed technology provides a surgical device adapted for use with a computerized surgical manipulation system, wherein the computerized surgical manipulation system includes a robotic arm, a support coupled to the robotic arm for receiving various instruments, and a motor housing coupled to the support, comprising an elongated shaft having a proximal end and a distal end a control housing coupled to the proximal end of the elongated shaft, wherein the control housing is configured to attach to the motor housing; an end effector coupled to the distal end of the elongated shaft, wherein the end effector includes a clamping mechanism having an anvil and a cartridge for containing surgical staples; and a trocar pivotally coupled to the support such that the trocar can pivot away from axial alignment with the support, wherein the distal end of the elongated shaft extends into the pivoted trocar, wherein the trocar is pivoted into axial alignment with the support, and wherein the control housing engages the motor housing.

The trocar includes a holding feature having an inner wall and an outer wall, wherein the holding feature of the trocar is pivotally coupled to the support through a gripping member, wherein an angled gap is formed between the gripping member and the inner wall when the trocar is axially aligned with the support, and wherein a second angled gap is formed between the gripping member and the outer wall when the trocar is pivoted away from axial alignment with the support. The control housing has a control interface with a plurality of platters, wherein the motor housing has a motor interface with a plurality of platters, and wherein the plurality of platters on the control interface selectively attaches to the plurality of platters on the motor interface to join the control housing and the motor housing.

It should be appreciated that all combinations of the foregoing concepts and additional concepts discussed in greater detail below (provided such concepts are not mutually inconsistent) are contemplated as being part of the technology disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the descriptions provided herein are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed technology and, together with the general description given above and detailed description given below, serve to explain the principles of the disclosed subject matter, and wherein:

FIGS. 8A-8B are illustrations of the trocar being held by a gripping member shown in FIG. 5, wherein FIG. 8A depicts the trocar in axial alignment with the support, and wherein FIG. 8B depicts the trocar pivoted away from axial alignment with the support;

FIGS. 9A-9C depict example progressions of inserting the surgical stapling device into the trocar, wherein FIG. 9A depicts inserting the surgical stapling device into the trocar pivoted away from axial alignment with the support, wherein FIG. 9B depicts the trocar pivoted into axial alignment with the support such that surgical device engages the motor housing, and wherein FIG. 9C depicts the control housing joined with the motor housing;

FIG. 19A-19B depicts example progressions of the firing mechanism, wherein FIG. 19A depicts example progressions of the firing mechanism moving within the surgical stapling device, and wherein FIG. 19B depicts example progressions of the beam of FIG. 16 delaminating;

FIG. 25A-25B depicts an example implementation of a bailout system, wherein FIG. 25A depicts the gear assembly of FIG. 21 in an engaged position, and wherein FIG. 25B depicts the gear assembly of FIG. 21 in a disengaged position.

DETAILED DESCRIPTION

Figure 1:
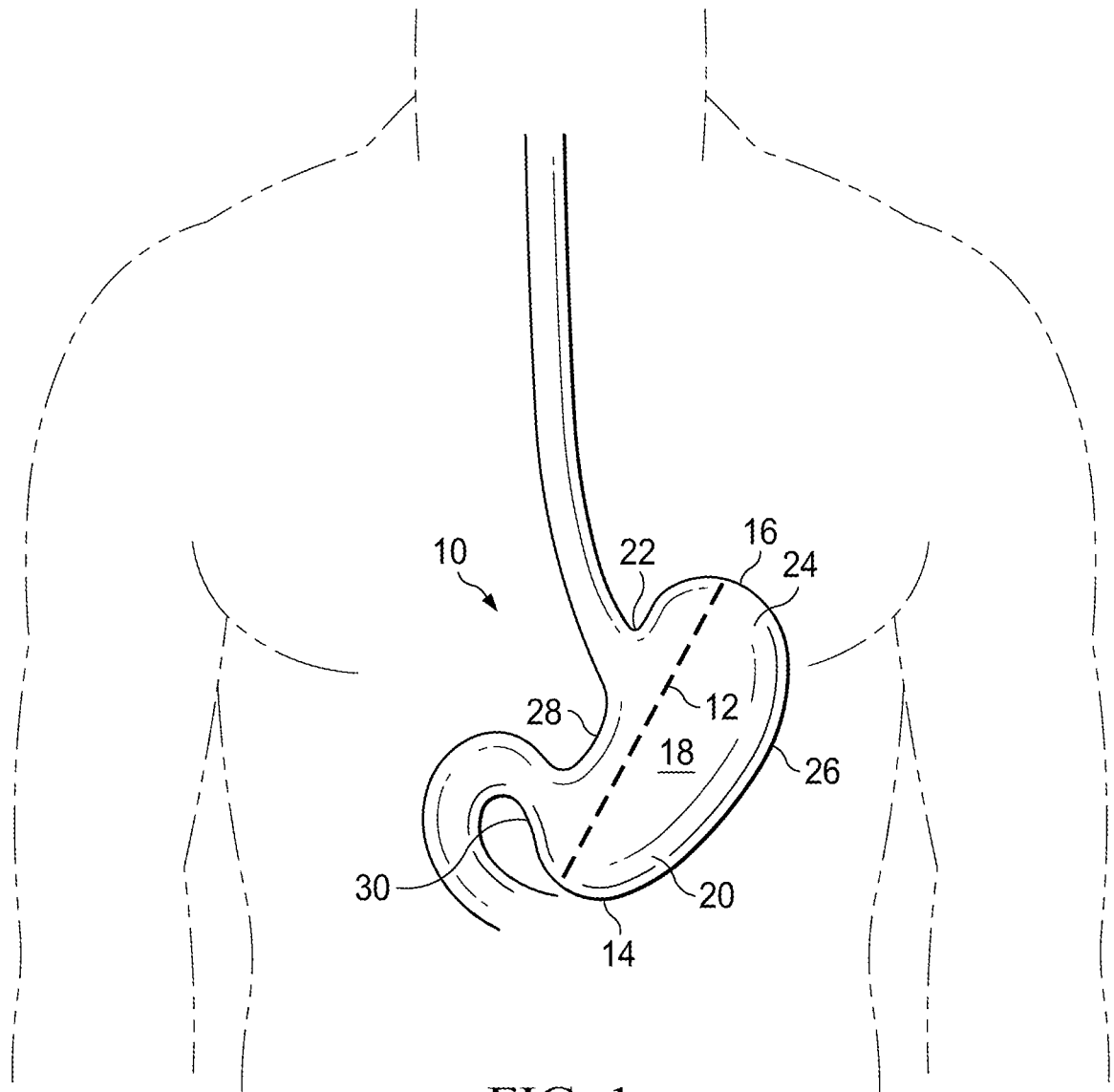
FIG. 1 depicts the anatomy of a stomach.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed technology. Accordingly, the following implementations are set forth without any loss of generality to, and without imposing limitations upon, the claimed subject matter.

The examples discussed herein are examples only and are provided to assist in the explanation of the apparatuses, devices, systems, and methods described herein. None of the features or components shown in the drawings or discussed below should be taken as required for any specific implementation of any of these the apparatuses, devices, systems or methods unless specifically designated as such. For ease of reading and clarity, certain components, modules, or methods may be described solely in connection with a specific Figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

U.S. Pat. No. 9,936,953 is relevant to the disclosed technology and is expressly incorporated by reference herein in its entirety and is made part of this patent application for all purposes. This reference discloses an end effector for use by a surgeon to staple an anatomical structure of a patient during minimally invasive procedures. The end effector comprises: (a) an anvil that includes a first end, a second end, and a face that is positionable on the first side of the anatomical structure; (b) a cartridge that is configured to house a plurality of staples and that includes a first end, a second end, and a face that is positionable on the second side of the anatomical structure; and (c) a flexible member that movably couples the first end of the anvil to the first end of the cartridge, wherein the anvil and the cartridge slidably receive the flexible member; wherein the second end of the anvil is movably coupled to the second end of the cartridge, each of the anvil and the cartridge is insertable through a trocar and the end effector is remotely operable from outside the patient with at least a portion of one of the anvil and the cartridge being movable toward the other to clamp the end effector to the anatomical structure.

Surgical instruments in accordance with the example implementations herein can be used in conjunction with a computerized surgical manipulation system, or also referred to as a robotic surgical system. In some example implementations, the computerized surgical manipulation system can include a surgeon's console, a patient cart, and a vision cart, wherein the vision cart can include a camera system and a plurality of robotic arms with supports that can each selectively receive various surgical instruments. The arms of some robotic surgical system have a series of joints to allow for a full range of movement of the arms during surgery. Example camera systems can include, for example, a dual lens optical system representing the left and right eyes. The spatial separation of these images can be projected to the surgeon's eyes in the binocular viewer to allow for true 3-D image perception at the console. Various instruments, such as the surgical instruments in accordance with the present disclosure, can be coupled to the various arms and are easily and rapidly changeable by the assistant surgeon or a trained scrub nurse at the patient side.

As described herein, surgical instruments and devices usable with computerized surgical manipulation systems can include a control housing, a drive system, and an end effector including a clamping mechanism. In one or more example implementation, the surgical instrument and device is a surgical stapling devices, wherein the clamping mechanism includes a cartridge and an anvil. During operation, via interaction with the surgical stapling devices via a surgical console, a surgeon can clamp the anvil and the cartridge on an organ or other tissue to compress the organ therebetween. Once the organ has been compressed, the surgeon can use the stapler to drive or fire staples through the organ. In one example implementation, a plurality of B-shaped staples can be formed. In another example implementation, the stapling device can be fired multiple times using multiple cartridges, or in an alternate implementation a single cartridge can be used with a single firing to complete resection of an organ. It may be advantageous to reduce the number of firings and cartridges required as the expense of a procedure can increase with the use of cartridges and with a longer procedure that can be associated with multiple stapler firings. It may also be advantageous to provide for single cartridge stapling and/or resection of an organ to reduce the time a patient is in surgery, which can improve clinical outcomes. For example, resecting a portion of the stomach in accordance with a sleeve gastrectomy procedure using a single cartridge and stapler firing may improve patient outcomes and reduce complications that can be associated with such procedures.

The integrity of a staple line can depend, in part, on the proper formation of the B-shaped staples, when such a staple configuration is desirable. Providing a single cartridge and single firing stapling device may improve the quality of staple formation over a device or system using multiple cartridges to complete the same procedure. For example, when using an end effector multiple times to staple and resect tissue, the previously deployed staples may be contacted by the new staples and/or cutting knife in subsequent applications. Providing a single cartridge and staple firing may help insure that the staple line, and the shape of the staples, is consistent.

A single cartridge and single firing stapling device may also provide compression benefits relative to a device and system requiring the use of multiple cartridges. It may be advantageous to provide a single firing stapling device that provide for desirable compression along the length of the tissue to be resected while also providing for a single staple line with properly formed staples. A B-shaped staple is the standard of care for gastrointestinal, vascular, pulmonary, and hepatic applications of surgical tissue fastening devices. Alignment in each of the X, Y, and Z axes of the clamping mechanism with itself (e.g., alignment of the anvil with the cartridge) on each side of the organ may improve staple delivery and formation. It will be appreciated that any suitable structure or mechanism may be incorporated into the stapling devices described herein to provide for such alignment.

Example implementations of the disclosed technology can be used, for example, in a sleeve gastrectomy procedure or resection of the stomach utilizing a computerized surgical manipulation system. It will be appreciated, however, that the devices and systems may be used in other procedures involving other anatomical structures. For example, the devices and systems may be used in a parenchymal resection, lung volume reduction surgery, or other procedures involving the lung. Further, example implementations of the disclosed technology may be useful in an anatomic resection, such as, a lobectomy, a non-anatomic parenchymal resection, or other procedures involving the liver, or in a partial nephrectomy, total nephrectomy, or other procedures involving the kidney.

FIG. 1 depicts the anatomy of stomach 10 and example resection line 12 for a vertical sleeve gastrectomy. Stomach 10 generally includes inferior end 14, superior end 16, anterior side 18, and posterior side 20. Gastroesophageal junction 22 opens into stomach 10 and is a common landmark in bariatric surgeries. Fundus 24 and the section of stomach 10 defined by greater curvature 26 are generally the parts of stomach 10 removed during a vertical sleeve gastrectomy. The remaining pouch or sleeve may be generally defined by lesser curvature 28 and resection line 12, which presents a stomach with a significantly reduced volume. The desired location of resection line 12 may be about 0.5 cm to about 2 cm away from gastroesophageal junction 22 and about 2 cm to about 10 cm away from pylorus 30. In accordance with implementations, computerized surgical manipulation systems 800 utilizing surgical stapling devices 100 described herein (shown in FIG. 5) may be utilized to form high quality, consistent resection lines during a vertical sleeve gastrectomy. Implementations of the devices may be advantageous because they may be easily positionable laparoscopically using robotic-assisted surgical techniques, can accommodate different thicknesses of tissue along the resection line length, can be capable of providing uniform compressive pressure on the tissue along the resection line, and can enable a low staple firing force.

Figure 2:
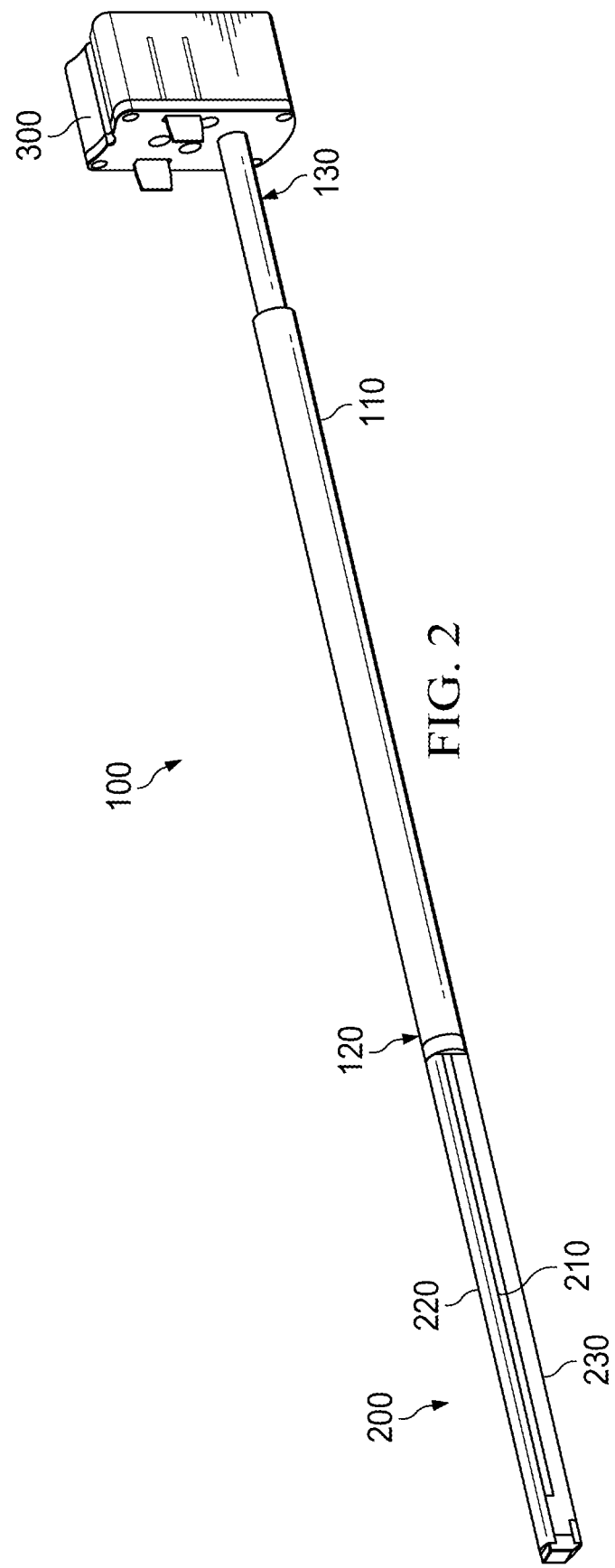
FIG. 2 depicts a surgical stapling device having an end effector and a control housing, in accordance with an example implementation of the disclosed technology.
Figure 3:
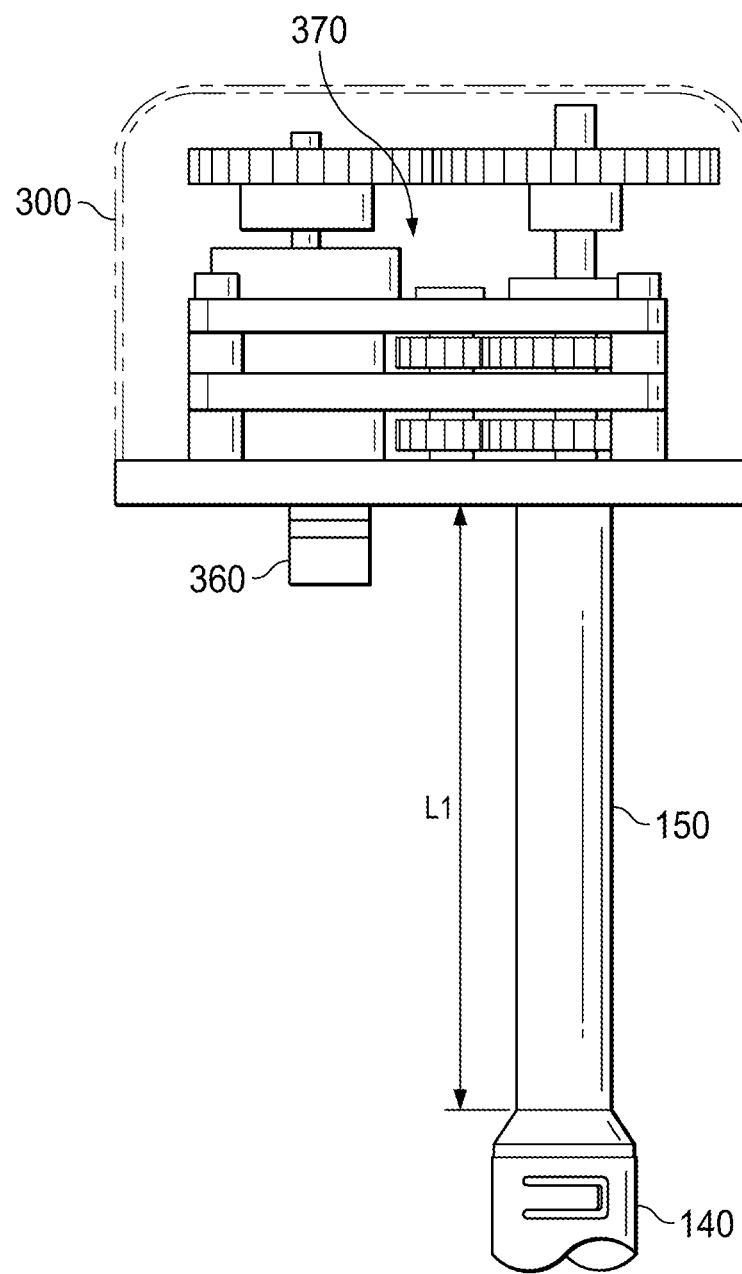
FIG. 3 depicts an example implementation of the control housing coupled to the surgical stapling device of FIG. 2.

With reference to FIGS. 2-3, surgical stapling device 100 includes elongated shaft 110 having distal end 120 and proximal end 130, end effector 200 positioned at distal end 120 of elongated shaft 110, and control housing 300 positioned at proximal end 130 of elongated shaft 110, wherein control housing 300 includes prongs 360 and gear assembly 370. In some implementations, control housing 300 further includes control interface 310 having first, second, and third rotatable platters 320, 330, 340, wherein each rotatable platter 320, 330, 340 includes recesses 350 (shown in FIG. 20). In one example implementation, end effector 200 includes clamping mechanism 210 having anvil 220 and cartridge 230 for holding a plurality of surgical staples. In one example implementation, elongated shaft 110 includes diameter portion 140 and reduced diameter portion 150, wherein the diameter of diameter portion 140 is greater than the diameter of reduced diameter portion 150, and wherein reduced diameter portion 150 of elongated shaft 110 is coupled to gear assembly 370 within control housing 300.

Figure 4:
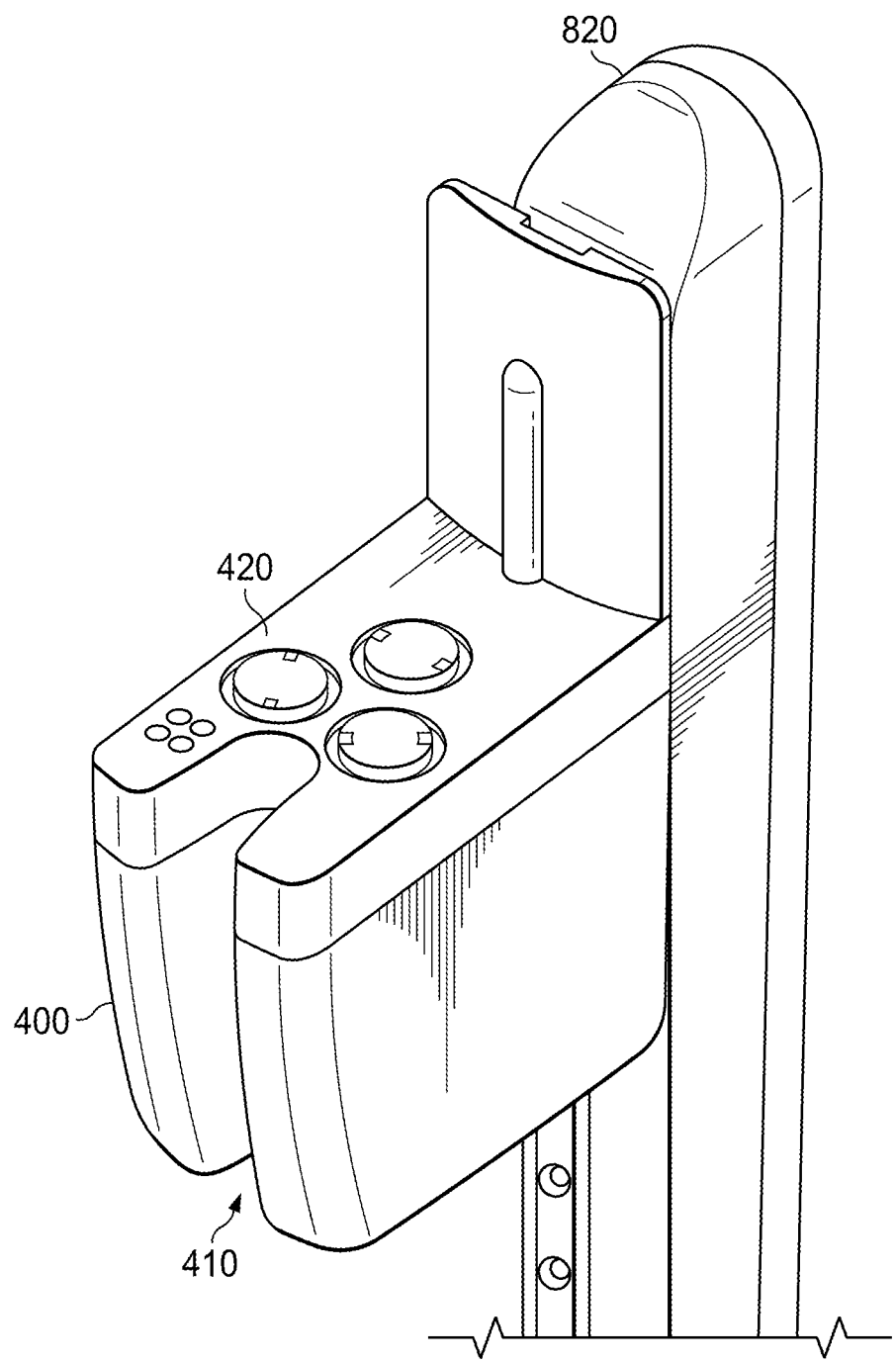
FIG. 4 depicts an example implementation of a motor housing coupled to a support.
Figure 5:
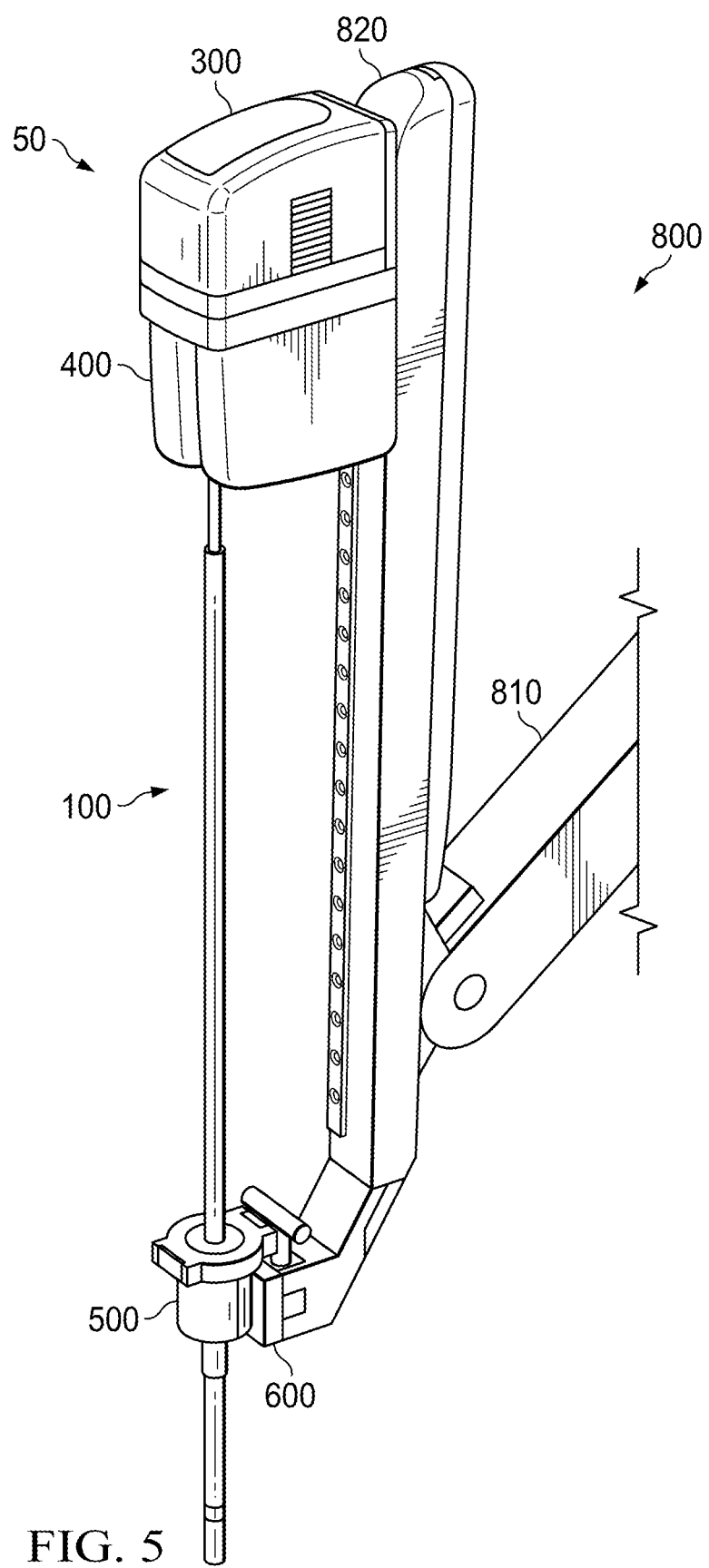
FIG. 5 depicts an assembled surgical system in use with computerized surgical manipulation system, in accordance with an example implementation of the disclosed technology, wherein the control housing of FIG. 2 is joined with the motor housing of FIG. 4.
Figure 6:
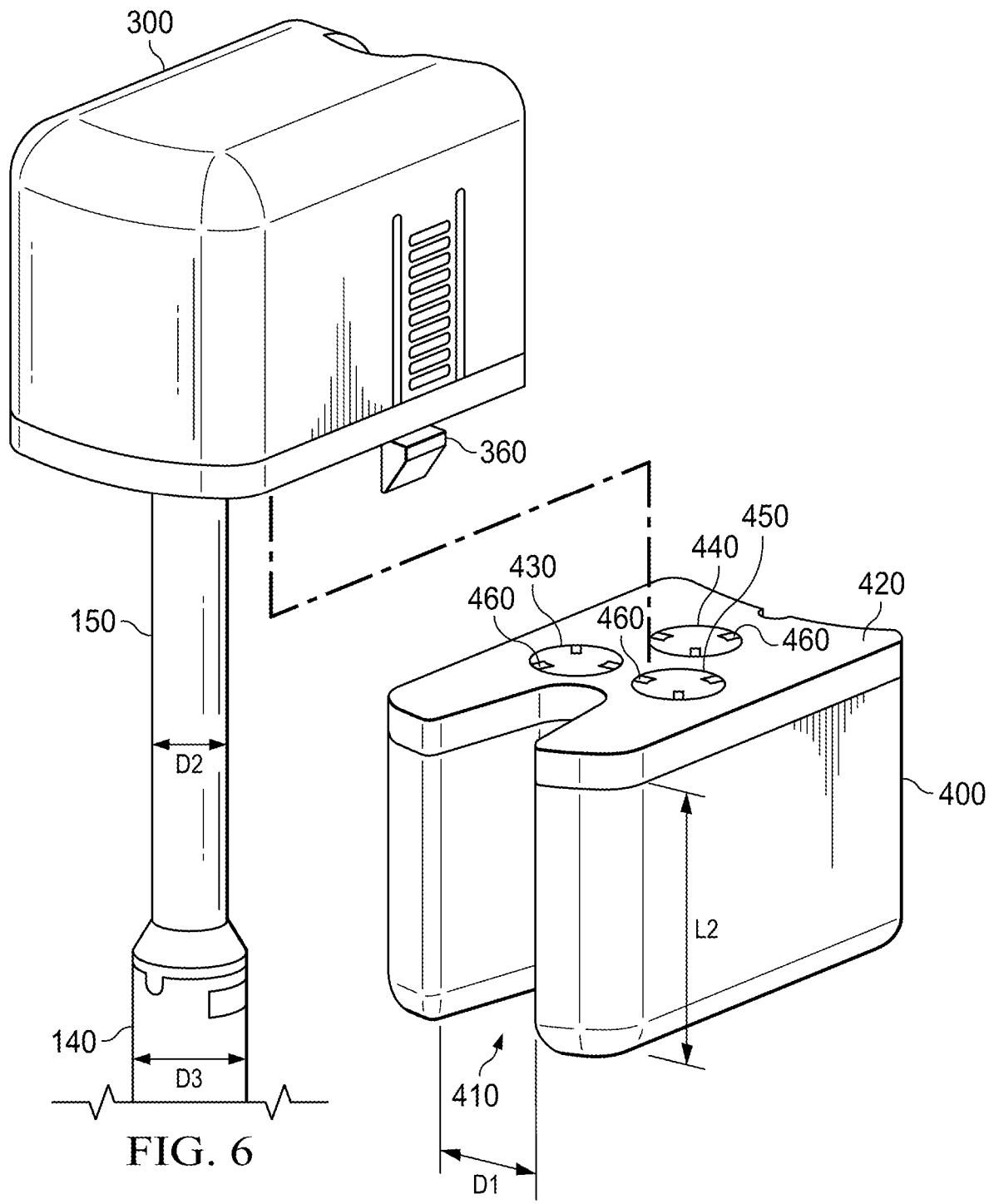
FIG. 6 depicts a perspective view of the motor housing of FIG. 4 receiving the surgical stapling device.

With reference to FIGS. 4-6, example surgical system 50 is adapted for use with computerized surgical manipulation system 800. In one implementation, surgical system 50 includes surgical stapling device 100 and trocar 500. In one implementation, computerized surgical manipulation system 800 includes robotic arm 810 having support 820 for holding motor housing 400 and gripping member 600, wherein motor housing 400 has notch 410, and wherein gripping member 600 can be a spring-loaded clip for holding trocar 500. Motor housing 400 further includes motor interface 420 having slots 470 for receiving prongs 360 of control housing 300 and having first, second, and third rotatable platters 430, 440, 450, wherein each rotatable platter 430, 440, 450 include projections 460. A plurality of high-speed, low torque motors can be positioned within motor housing 400 that be used to drive the various mechanical functions of surgical stapling device 100.

With reference to FIG. 6, notch 410 extends the length L2 of motor housing 400 and is configured to receive elongated shaft 110 of surgical stapling device 100. In the illustrated implementation, notch 410 has a width of approximately 12 mm, which is shown as diameter D1. Reduced diameter portion 150 extends distally from control housing 300, wherein reduced diameter portion 150 can be specifically sized to fit within notch 410. In the illustrated implementation, reduced diameter 150 has a diameter D2, which is less than the diameter D1 of notch 410, and diameter portion 140 has a diameter D3, which is greater than the diameter D1 of notch 410. Reduced diameter 150 allows for elongated shafts larger than diameter D1 of notch 410 to be installed in surgical system 50 without having to reconfigure the mechanical mechanisms (closure mechanism 1000 and firing mechanism 1110 discussed below) of surgical stapling device 100. In one implementation, the length of reduced diameter portion 150 (shown as L1 in FIG. 3) is longer than length L2 of notch 140 for allowing control housing 300 to attach to motor housing 400.

Figure 7:
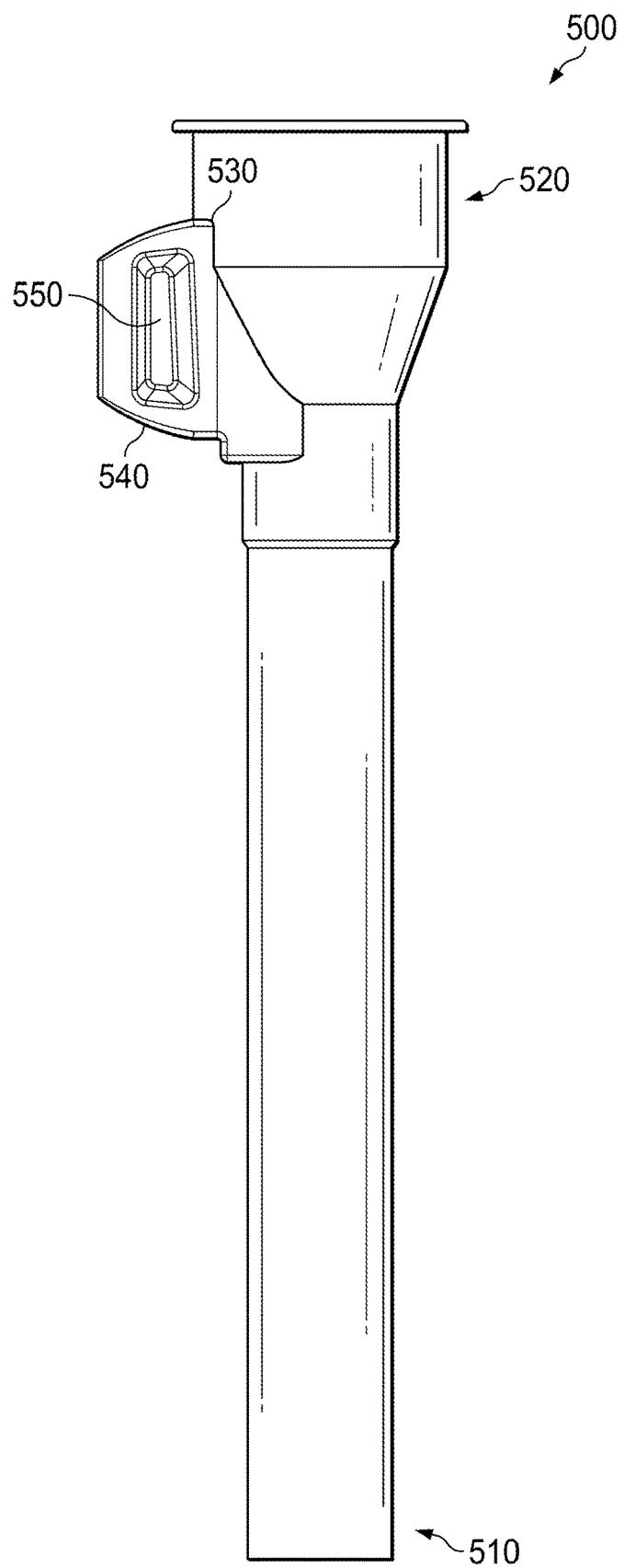
FIG. 7 depicts an example implementation of a trocar component of the surgical system of FIG. 5.
Figure 8A:
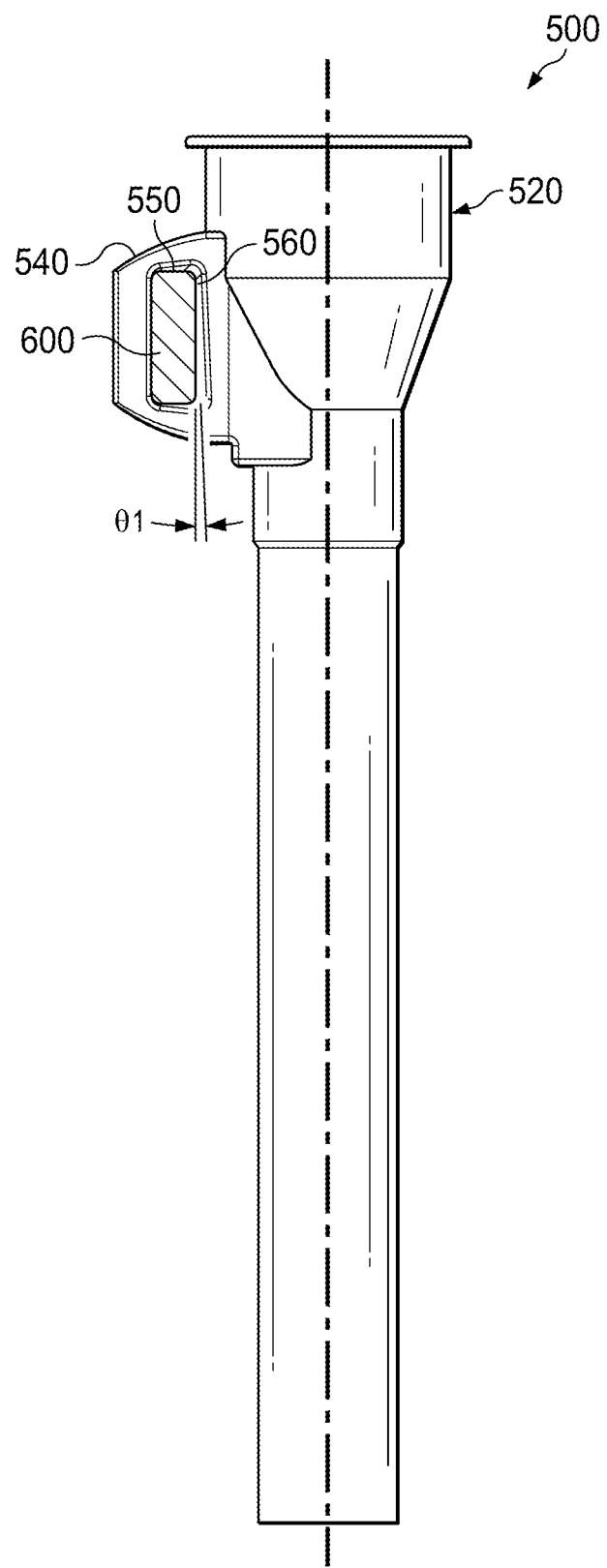
Figure 8B:
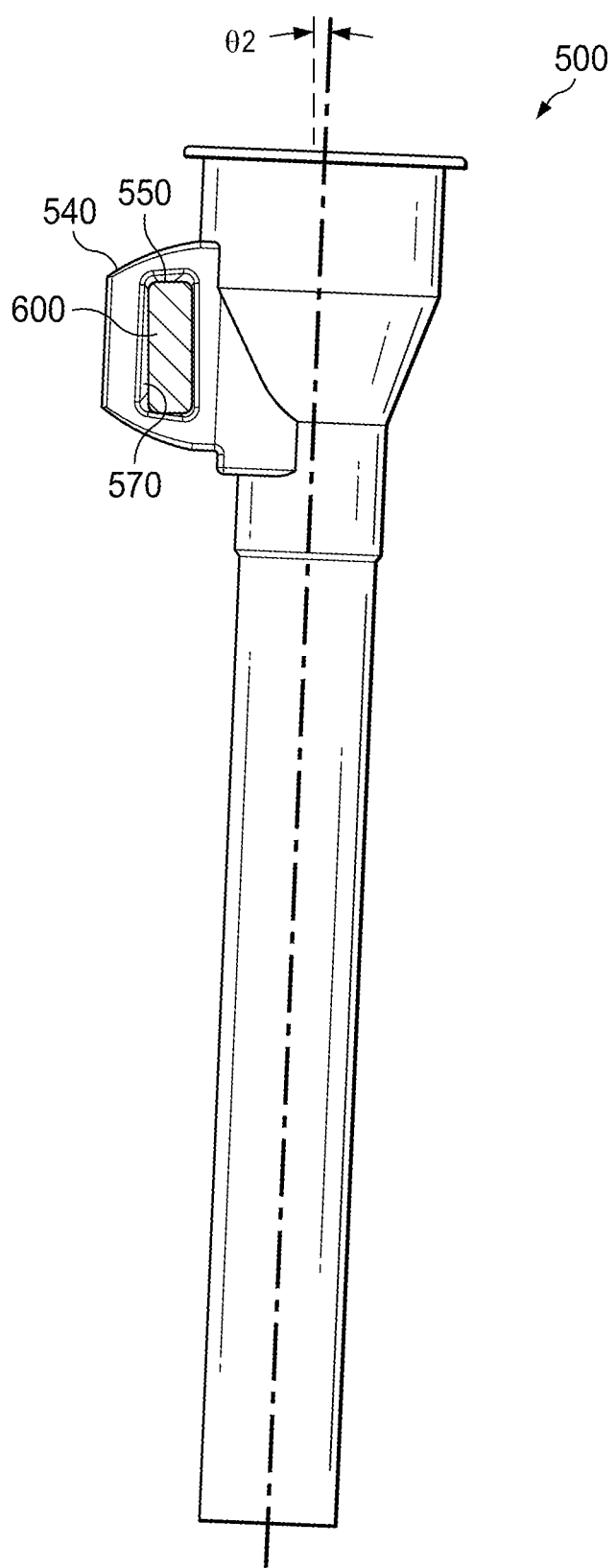

FIGS. 5, 7, and 8A-8B depict trocar 500 for use in surgical system 50. FIG. 7 illustrates trocar 500 having distal end 510, proximal end 520, and trocar surface 530, wherein holding feature 540 extends outward from trocar surface 530. In the illustrated implementation, holding feature 540 can be located proximate to proximal end 520 of trocar 500 and define a pair of recesses 550 that are positioned on opposing sides of holding feature 540. The geometry of recesses 550 allow for the desired pivoting action of trocar 500. More specifically, the geometry of the recesses 550 allow for trocar 500 to slightly move or pivot relative to gripping members 600, with the degree of movement confined by inner wall 560 and outer wall 570 of recess 550. FIGS. 5 and 8A-8B illustrate trocar 500 pivotally coupled to gripping members 600. When trocar 500 is axially aligned with support 820 of robotic arm 810, angled gap 01 is formed between gripping member 600 and inner wall 560 of recess 550 (shown in FIG. 8A). In one example implementation, holding feature 540 can be biased to maintain trocar 500 in its axially aligned position with support 820. Pivoting or tilting trocar 500 away from axial alignment with support 820 brings inner wall 560 in contact with gripping member 600 and forms second angled gap 02 between gripping member 600 and outer wall 570 of recess 550 (shown in FIG. 8B). It is to be appreciated that the amount of tilt provided by trocar 500 can vary based on implementation, but in some example implementations, trocar 500 is tiltable from 0 degrees to about 10 degrees, although this disclosure is not so limited.

Figure 9A:
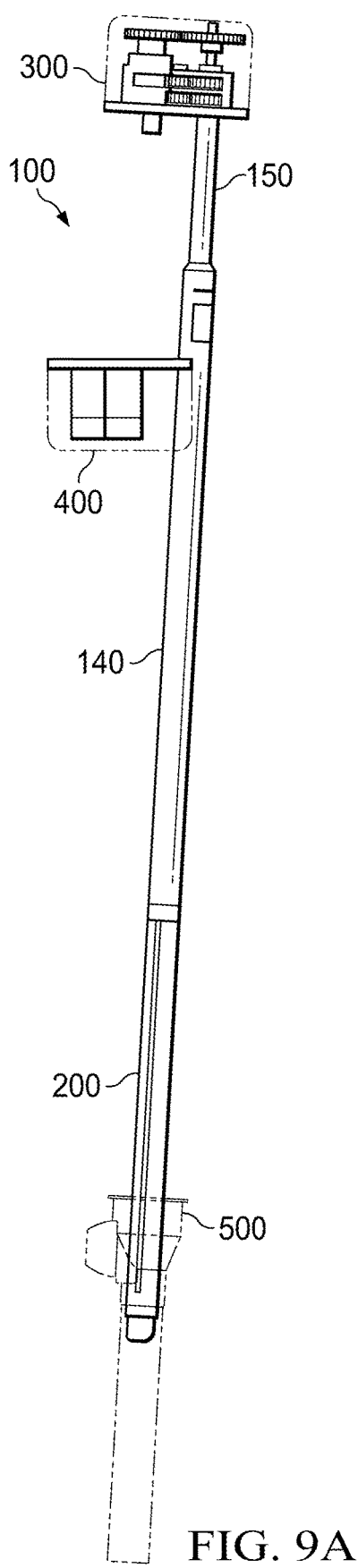
Figure 9B:
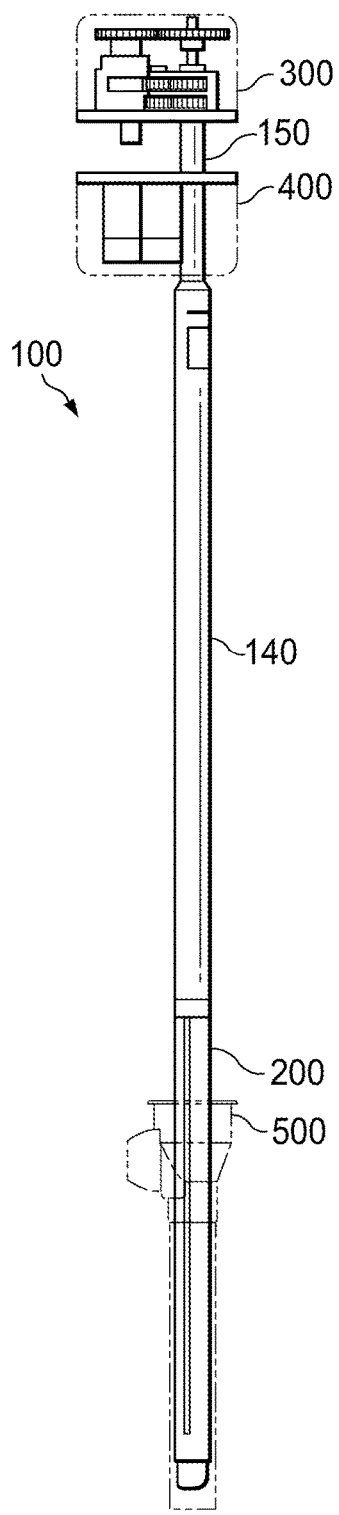
Figure 9C:
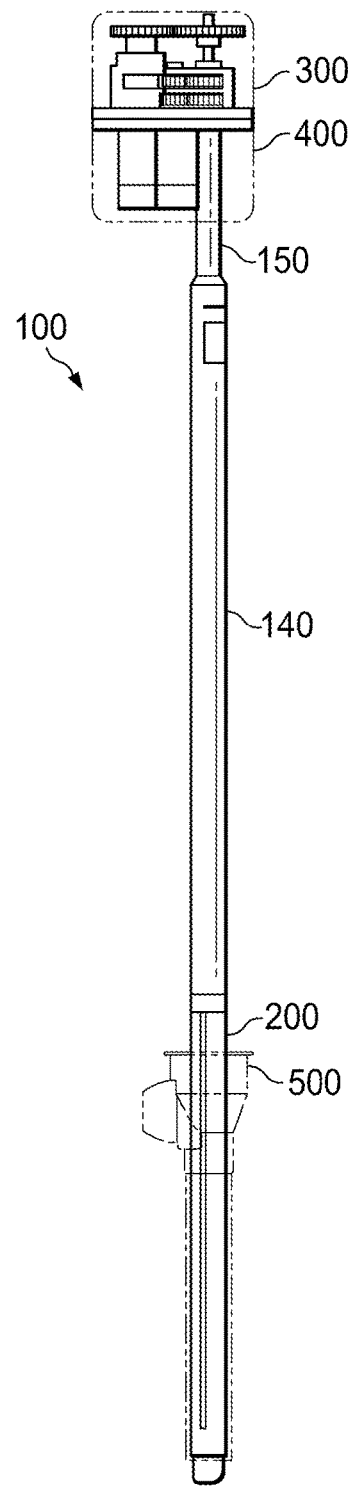
Figure 10:
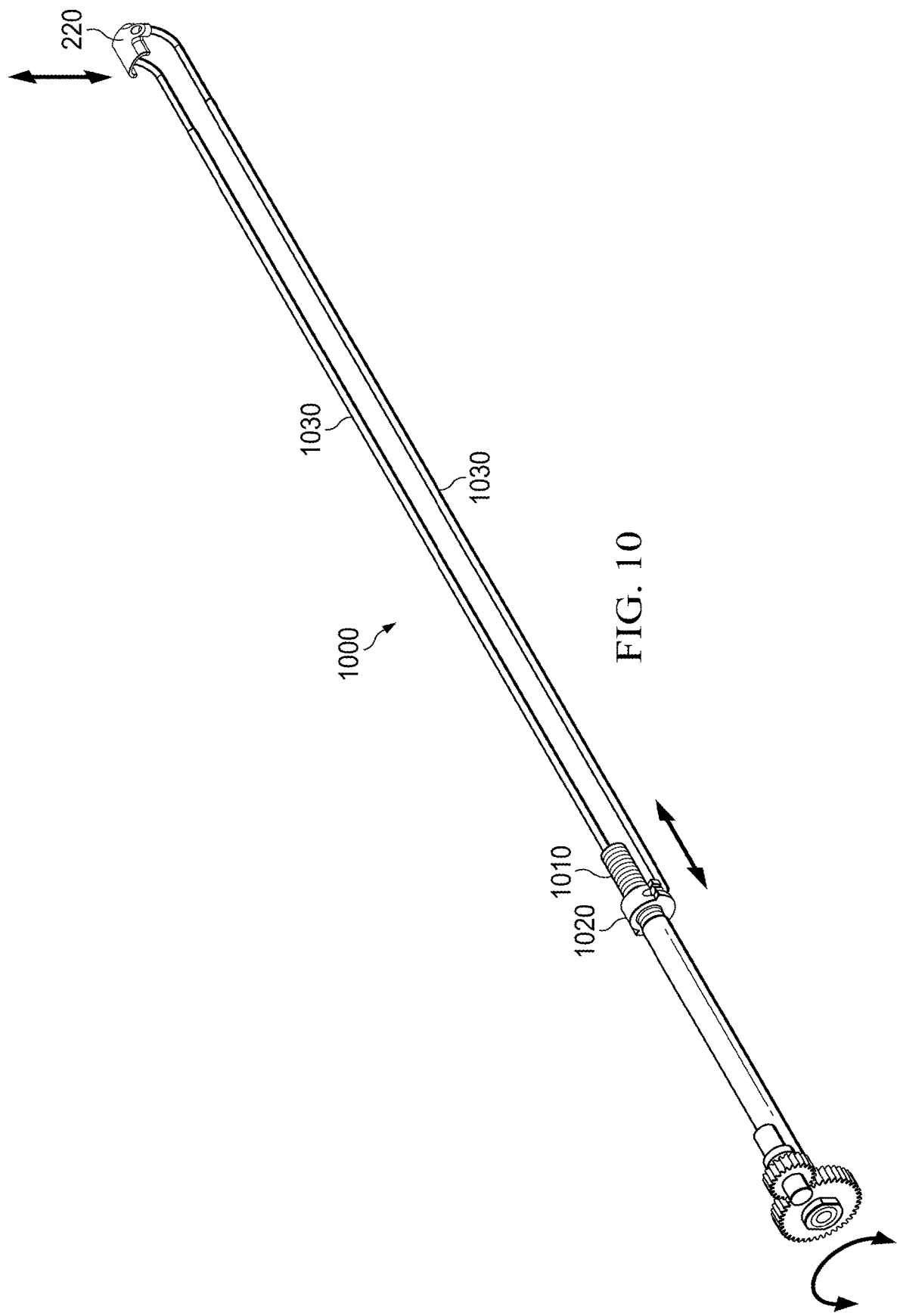
FIG. 10 depicts an example implementation of a closure mechanism for opening and closing an anvil on the end effector.
Figure 11:
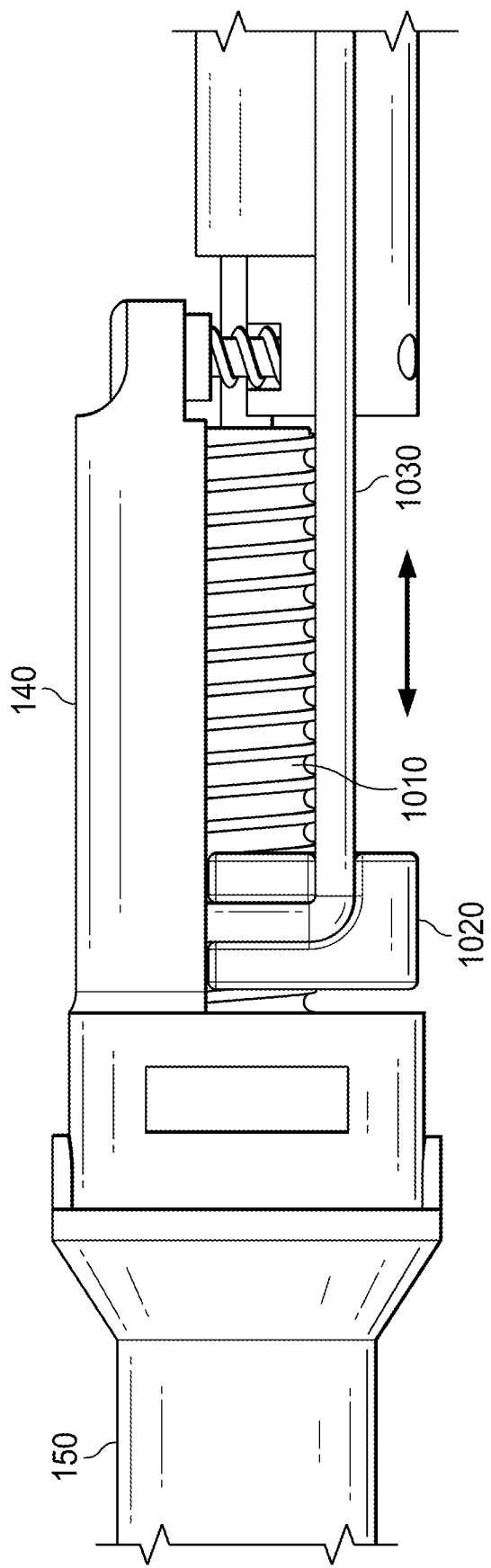
FIG. 11 depicts a side view of the closing mechanism of FIG. 10 housed within the surgical device.
Figure 12:
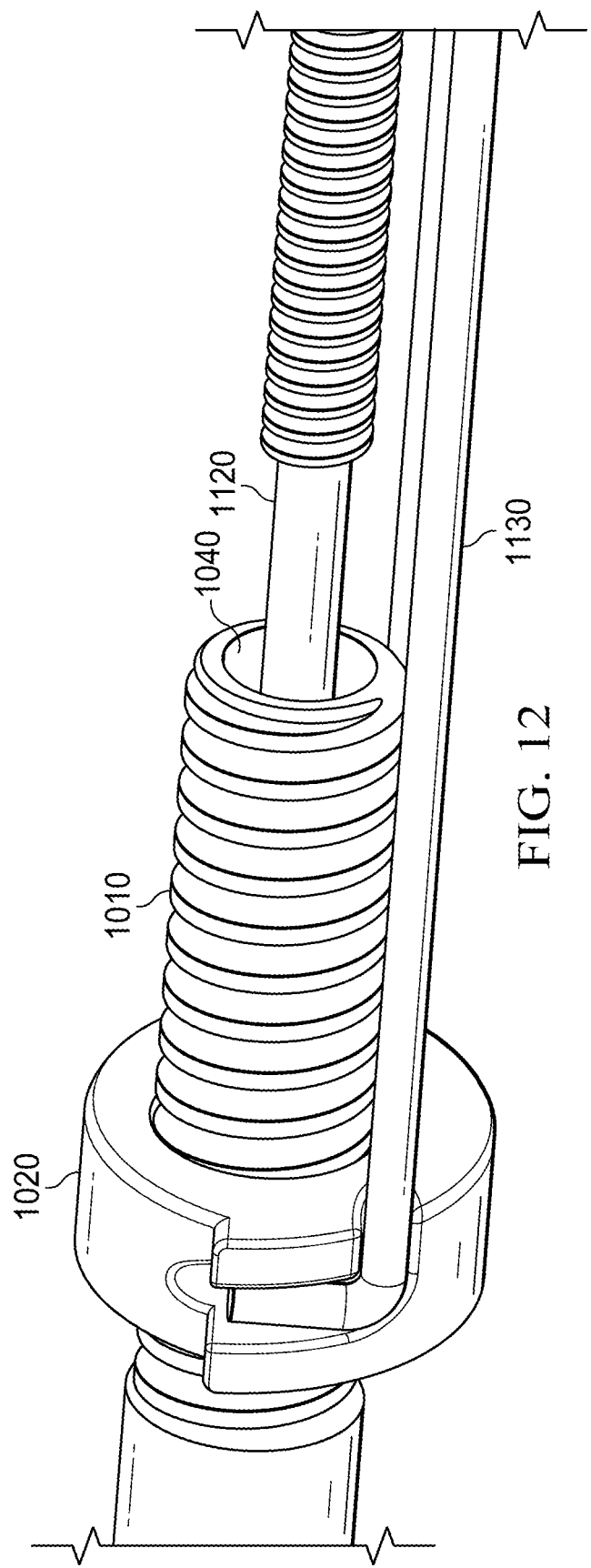
FIG. 12 depicts an example implementation of a follower nut component of the closing mechanism of FIG. 10 having a hollow cavity.
Figure 13:
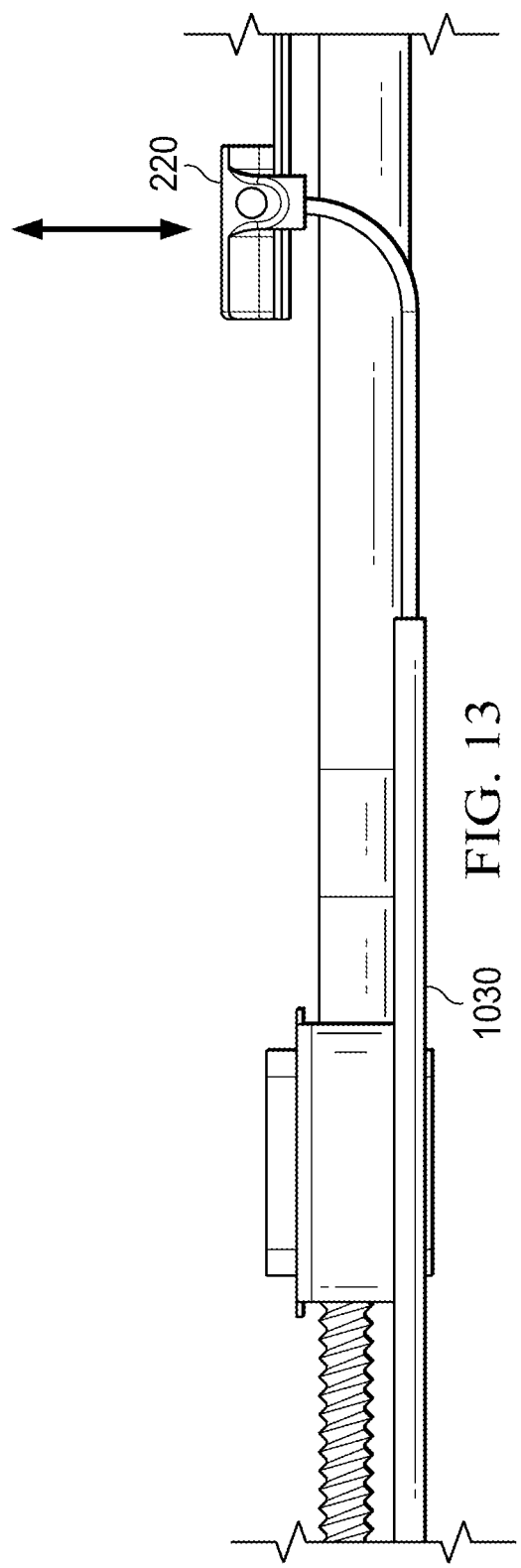
FIG. 13 depicts a side view of an example implementation of a control member of the closing mechanism of FIG. 10 for opening and closing the anvil.

FIGS. 9A-9C schematically illustrate an example progression of inserting surgical stapling device 100 having end effector 200 into trocar 500 when slightly pivoted away from axial alignment. To insert surgical stapling device 100 into trocar 500, trocar 500 can outwardly pivot to initially accept distal end 120 coupled with end effector 200 through proximal end 520 (shown in FIG. 9A). In the illustrated implementation, surgical stapling device 100 is distally advanced into trocar 500 until reduced diameter portion 150 can be received into notch 410 of motor housing 400. Trocar 500 containing surgical stapling device 100 then pivots back towards axial alignment with support 820, and reduced diameter portion 150 secures into notch 410 of motor housing 400 (shown in FIG. 9B). During a surgical procedure, trocar 500 can be coupled to support 820 or to robotic arm 810 of computerized surgical manipulation system 800, and advancement of surgical stapling device 100 through trocar 500 can be effected by, for example, the linear translation of motor housing 400 relative to trocar 500. Control housing 300 can then be lowered onto motor housing 400 such that control interface 310 and motor interface 420 mate (shown in FIG. 9C), or motor housing 400 can be raised to control housing 300. More specifically, recesses 350 on first, second, and third rotatable platters 320, 330, 340 of control interface 310 receive projections 460 on first, second, and third rotatable platters 430, 440, 450 of motor interface 420. It is to be appreciated that the particular configuration of control interface 310 can vary based on the configuration of motor interface 420. Prongs 360 then engage slots 470 to secure control housing 300 with motor housing 400. It is to be appreciated that surgical system 50 and surgical stapling device 100 can be used with trocars that do not necessarily include a tilting feature.

FIGS. 10-13 depicts an example implementation of closure mechanism 1000 for opening and closing anvil 220 on end effector 200. Closure mechanism 1000 is housed within elongated shaft 110 and includes drive screw 1010 having hollow cavity 1040 and follower nut 1020 in threaded engagement therewith. Rotation of drive screw 1010 causes follower nut 1020 to translate proximally or distally through elongated shaft 110, depending on the direction of rotation of drive screw 1010. In the illustrated implementation, one or more control members 1030 are coupled to follower nut 1020 and anvil 220. In another example implementation, control members 1030 can comprise a rigid portion and a flexible portion, wherein the flexible portion can be captured within a conduit of elongated shaft 110 to avoid or reduce undesirable buckling. As follower nut 1020 is distally translated by rotation of drive screw 1010, control members 1030 push anvil 220 open. As follower nut 1020 is proximally translated by rotation of drive screw 1010, control members 1030 pull anvil 220 closed.

Figure 14:
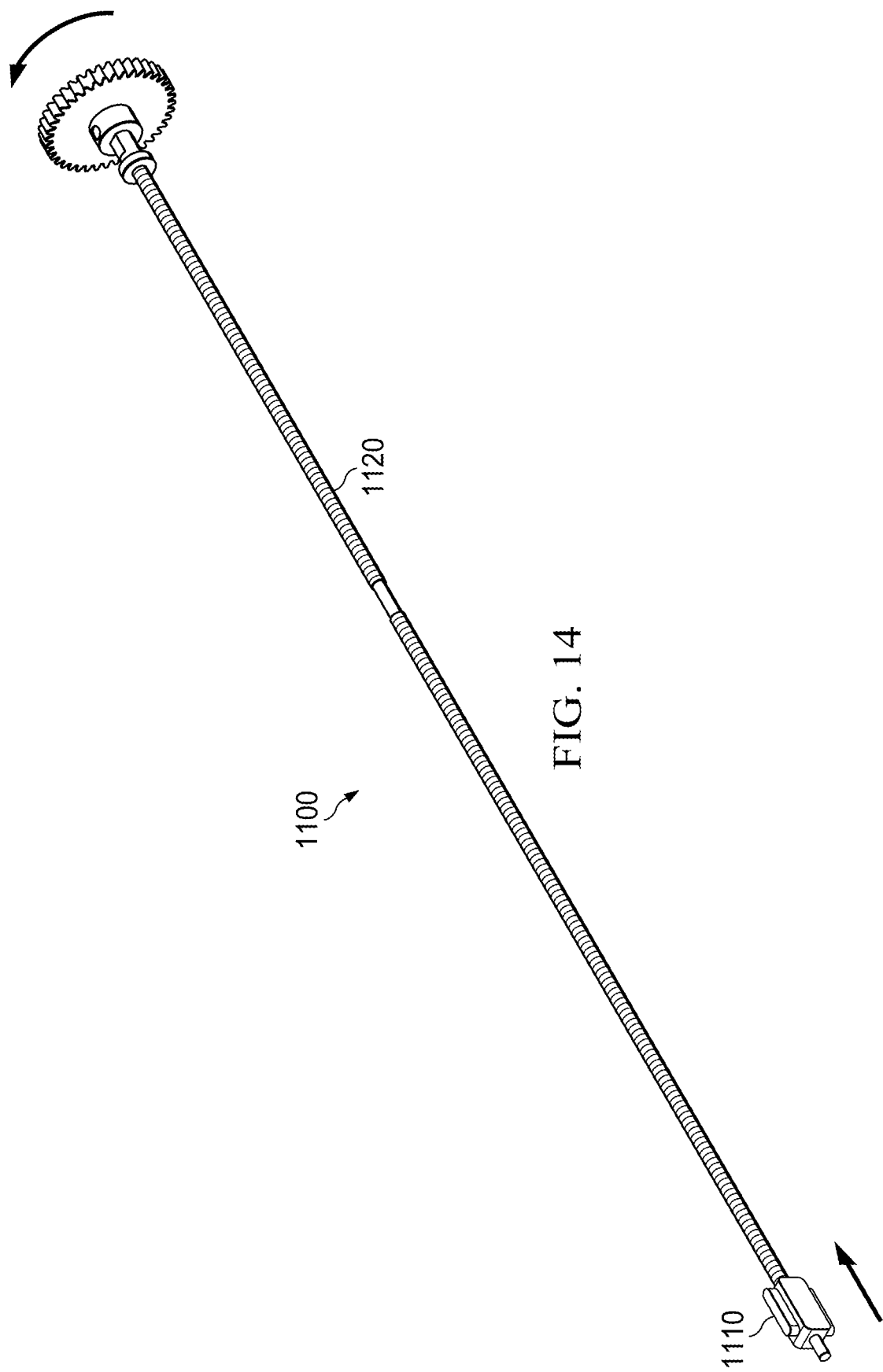
FIG. 14 depicts an example implementation of a firing mechanism.

With reference to FIG. 14, firing mechanism 1100 of surgical stapling device 100 comprises nut 1110 threadedly coupled to rotating member 1120, wherein rotating member 1120 is coaxial with nut 1110. In the illustrated implementation, rotating member 1120 is positioned within hollow cavity 1040 of drive screw 1010 such that drive screw 1010 and rotating member 1120 are axially aligned and co-radial, while being able to rotate independently. During a surgical procedure, nut 1110 can initially start at a distal position, and during firing of surgical stapling device 100, nut 1110 can be proximally translated through rotation of rotating member 1120.

Figure 15:
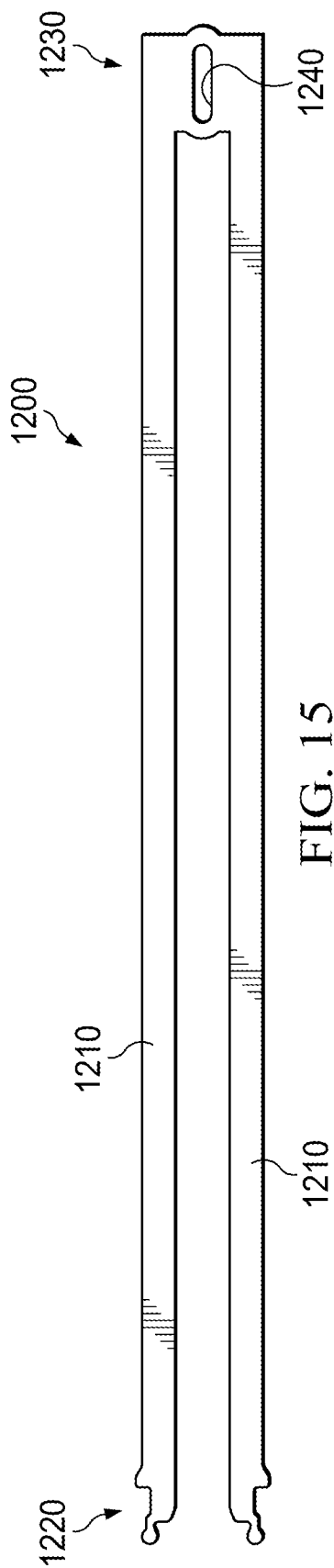
FIG. 15 depicts an example implementation of a beam component of the firing mechanism of FIG. 14, wherein the beam is shown in a flat configuration.
Figure 16:
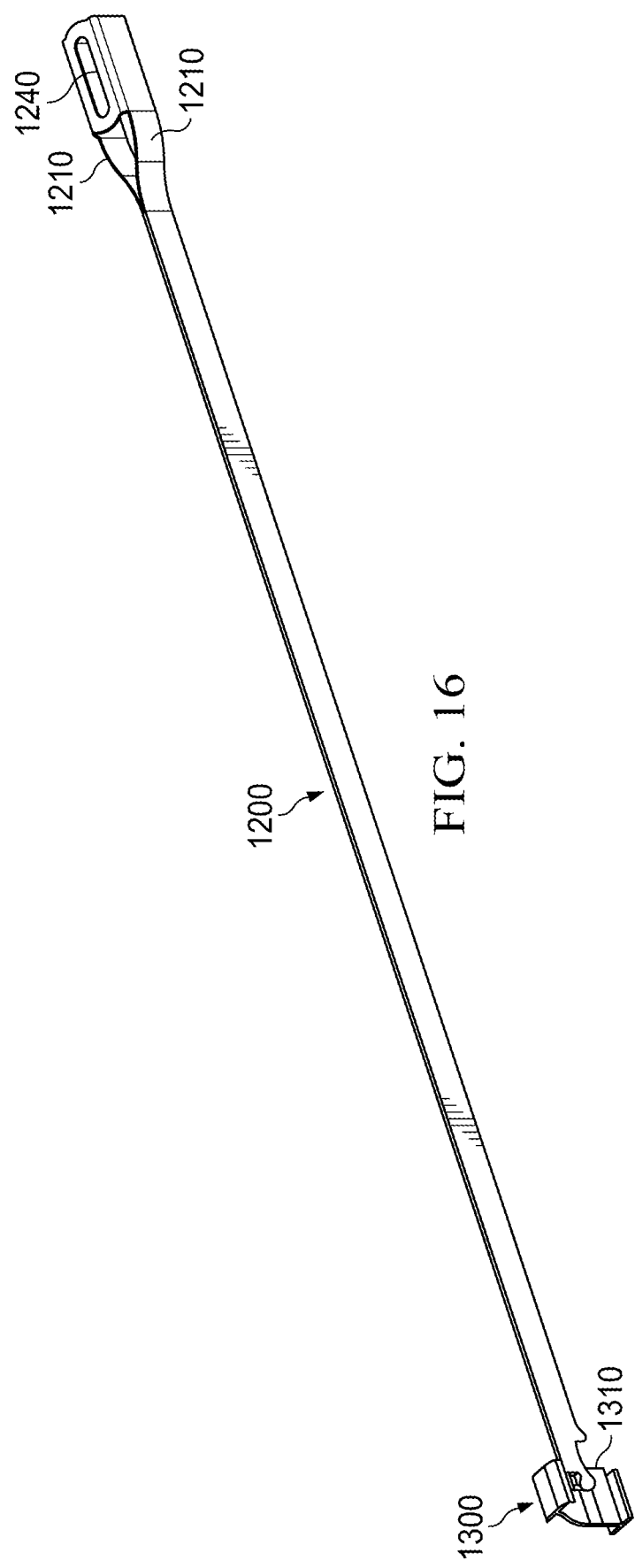
FIG. 16 depicts a perspective view of the beam of FIG. 15, wherein the beam is shown in a folded, laminate configuration with a blade coupled to a distal end of the beam, according to one example implementation.

With reference to FIGS. 15-16, firing mechanism 1100 may further comprise beam 1200 and blade 1300. FIG. 15 depicts example beam 1200 in a flat, laid-out configuration, wherein beam 1200 includes bands 1210, distal end 1220, proximal end 1230, and aperture 1240, wherein proximal end 1230 defines aperture 1240 that receives nut 1110. In one implementation, beam 1200 can be stamped from ½ to ¾ hard 300 series stainless steel, for example, and then folded to form the desired operational shape. FIG. 16 depicts example beam 1200 in an example elongated folded, laminate configuration, wherein bands 1210 are mirrored, and wherein blade 1300 having cutting edge 1310 is coupled to distal end 1220 of beam 1200. Blade 1300 can be coupled to distal end 1220 via any suitable attachment technique, such as a seam weld, spot welds, or combinations thereof.

Figure 17:
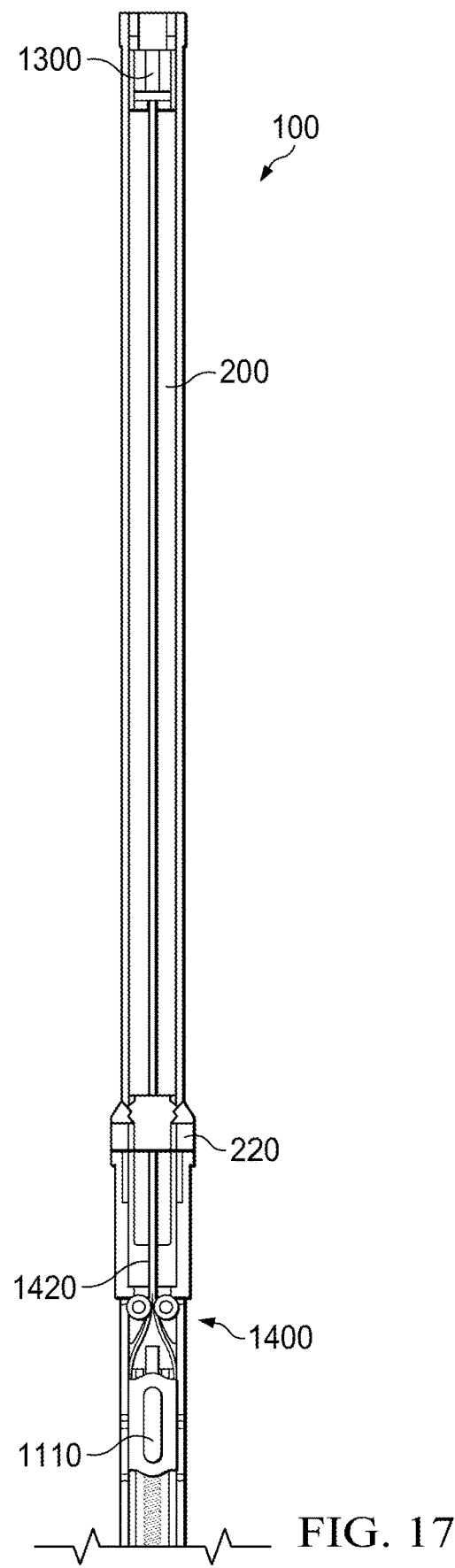
FIG. 17 depicts a top, cross-sectional view of the surgical stabling device of FIG. 2, showing the firing mechanism of FIG. 14 and the beam of FIG. 16 assembled in the surgical stapling device, according to one example implementation.
Figure 18:
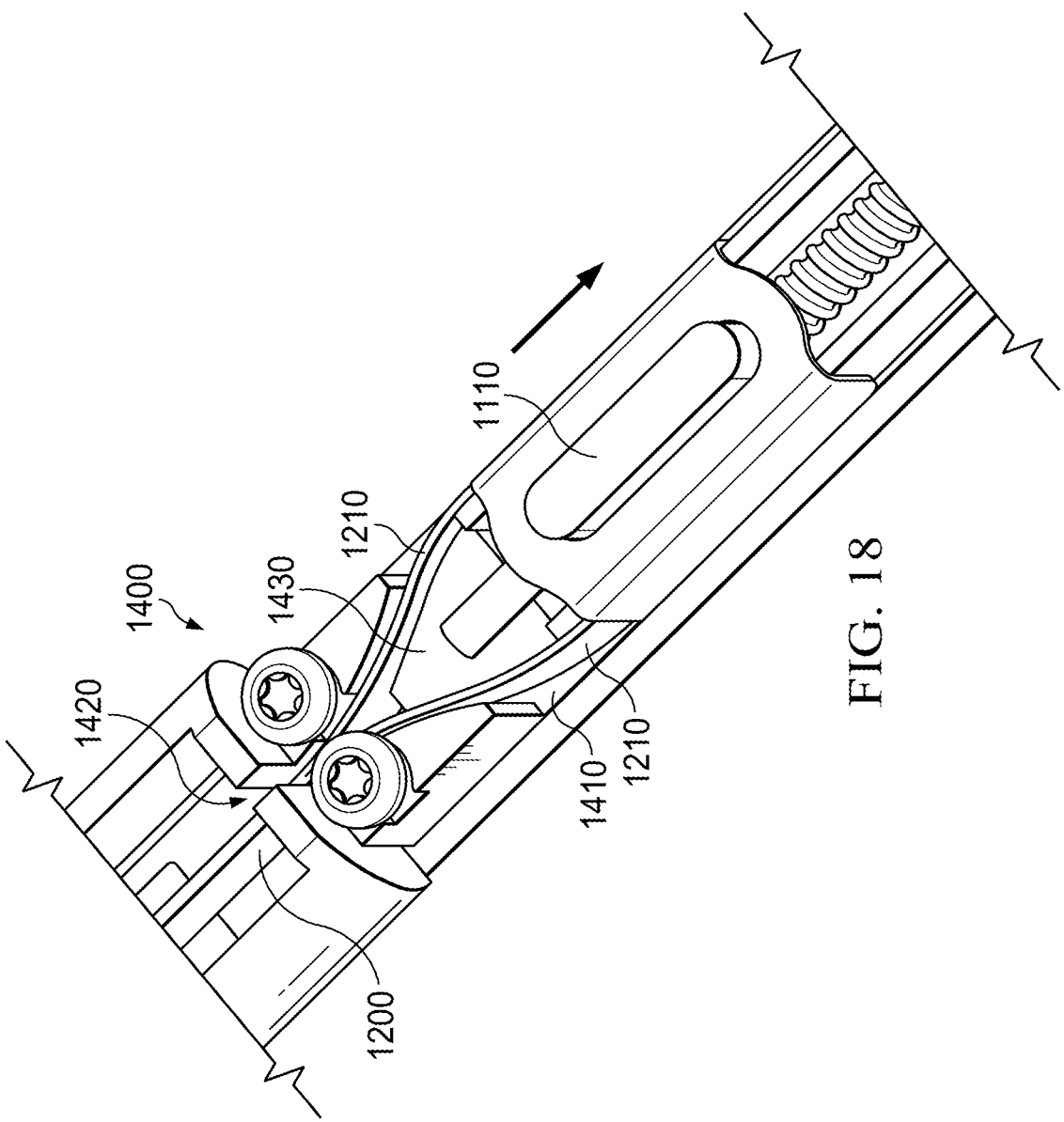
FIG. 18 depicts an example implementation of a band splitting portion housed within the surgical stapling device, wherein a central channel and divisional channels are shown according to one example implementation.

FIGS. 17-18 depict firing mechanism 1100 configured within surgical stapling device 100, according to one example implementation. Elongated shaft 110 of surgical stapling device 100 can define band splitting portion 1400 that includes band splitter 1430 and two diversion channels 1410 that each laterally divert from central channel 1420. The laminate portion of beam 1200 is located in central channel 1420 such that blade 1300 is positioned at the distal end of end effector 200. Band splitting portion 1400 is positioned proximally to the proximal end of rotating member 1120 such that nut 1110 engages aperture 1240, allowing bands 1210 of beam 1200 to be delaminated and diverted into diversion channels 1410 as nut 1110 travels along rotating member 1120.

Figure 19A:
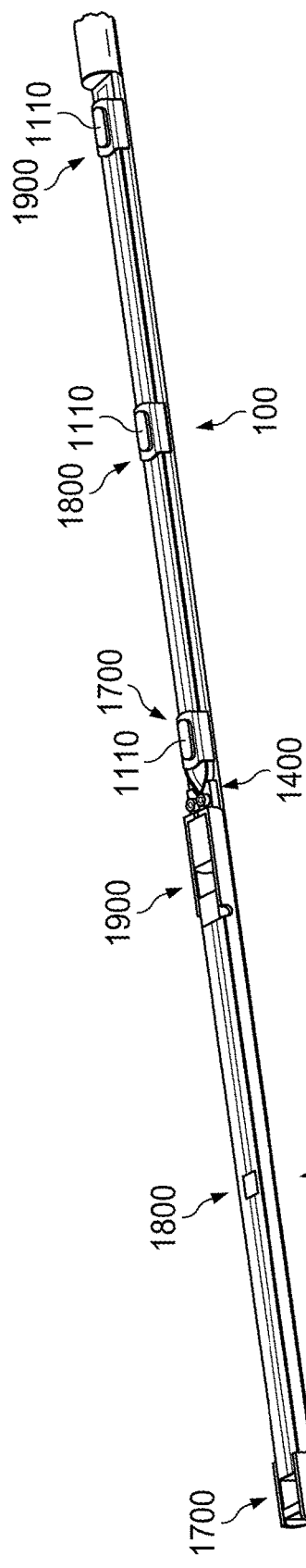
Figure 19B:
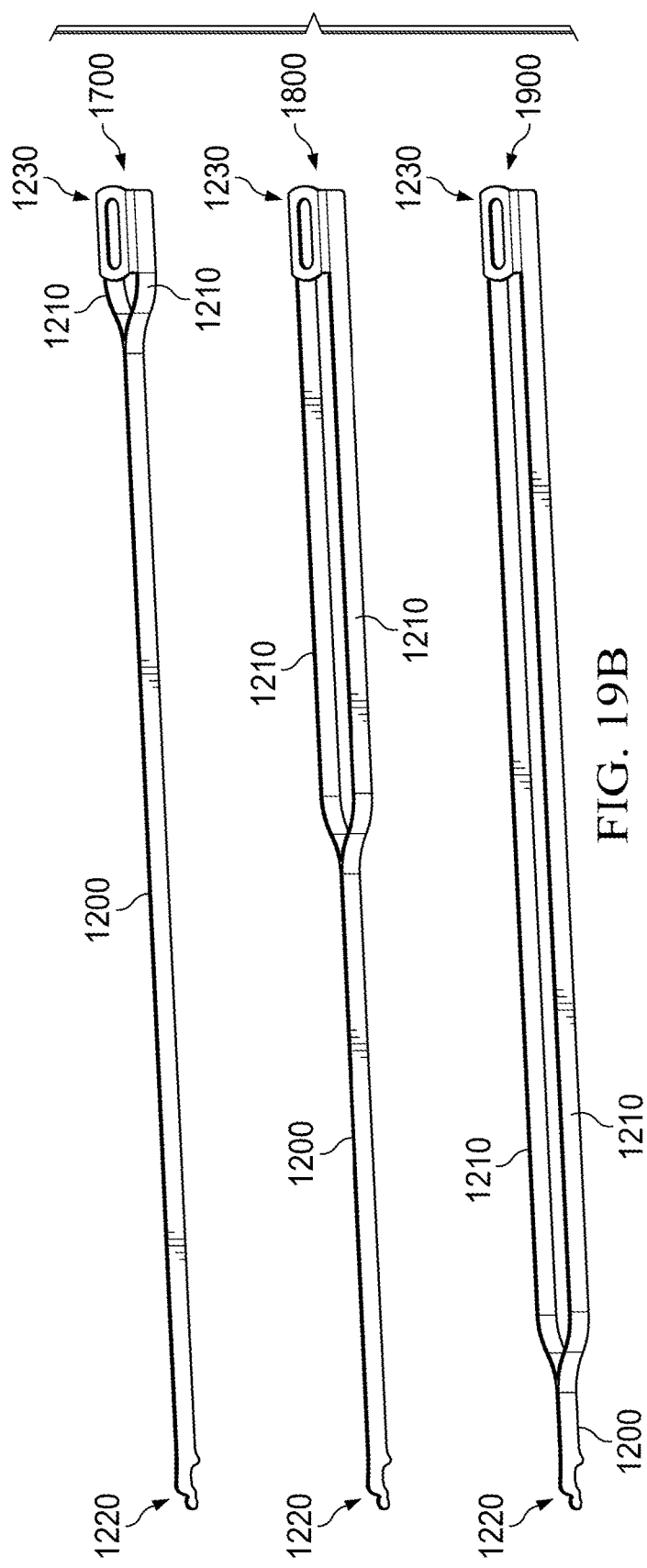

FIGS. 19A-19B depict de-lamination of beam 1200 at three different operational positions 1700, 1800, 1900 during operation of surgical stapling device 100. As surgical stapling device 100 is activated, nut 1110 is urged proximally along rotating member 1120 causing beam 1200 and blade 1300 to correspondingly move in a proximal direction. As blade 1300 is urged proximally, cutting edge 1310 can transect tissue and surgical staples from cartridge 230 can be inserted into the tissue. At first operational position 1700, nut 1110 and blade 1300 are both in their distal-most positions. At second operational position 1800, nut 1110 has proximally advanced, causing a portion of beam 1200 to pass through band splitting portion 1400 and divert into diversion channels 1410. At third operational position 1900, nut 1110 and blade 1300 are both in their proximal-most positions, and bands 1210 of beam 1200 have been almost fully separated or de-laminated by band splitter 1430. It will be appreciated that beam 1200 can include a single band, instead of having mirrored bands 1210. In such an implementation, the single band can be routed to one side of nut 1110 through one of diversion channels 1410.

With reference to FIGS. 19A-19B, the direction of rotation of rotating member 1120 can be reversed in a bailout situation (shown in FIGS. 25A-25B) to distally translate nut 1110. As nut 1110 translates distally along rotating member 1120, beam 1200 will travel through band splitting portion 1400 in the reverse direction (from third operational position 1900 to first operational position 1700) and be returned to its laminated configuration.

Figure 20:
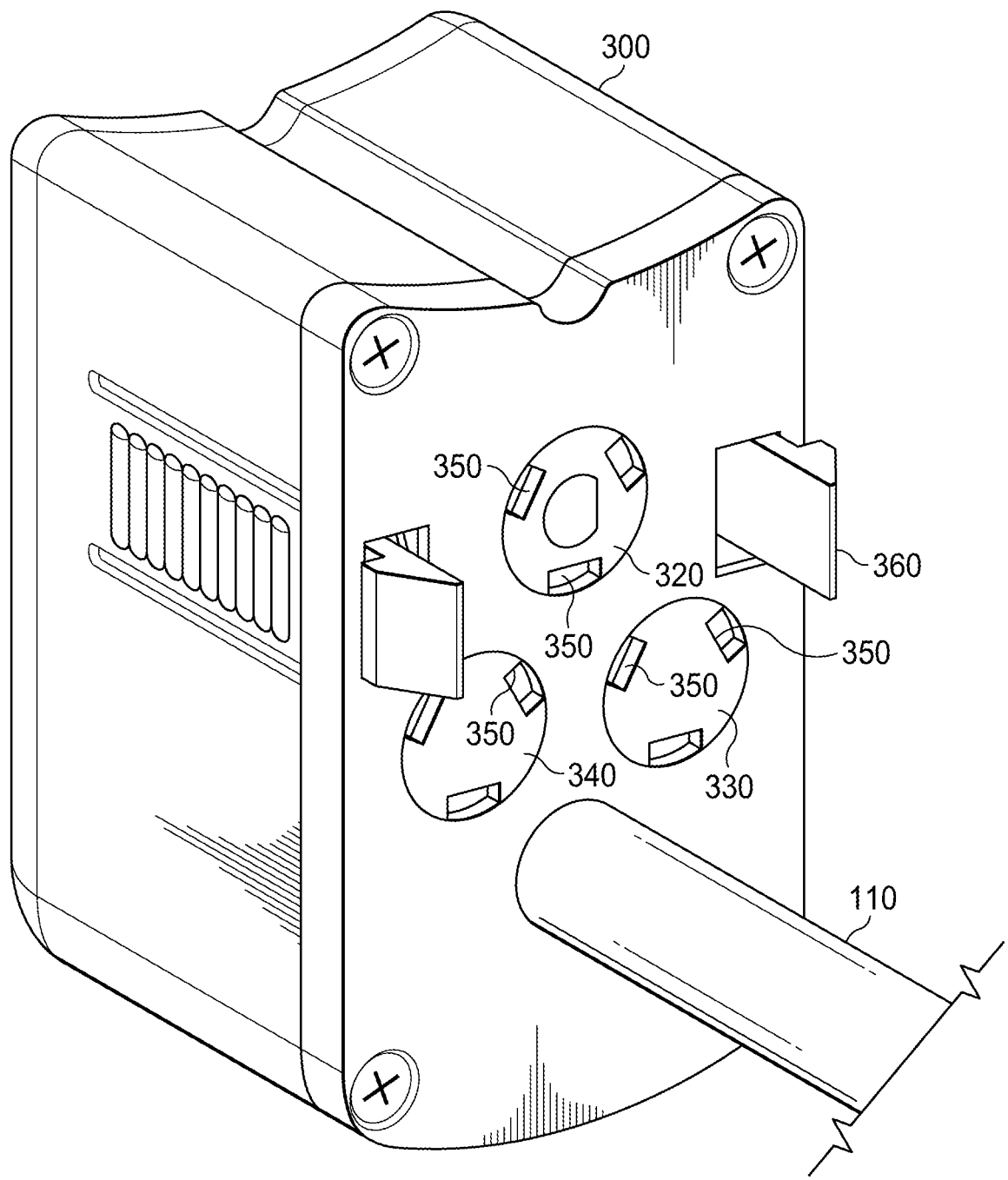
FIG. 20 depicts a perspective view of the control housing of FIG. 3, showing the control housing having a first, second, and third rotatable platter, according to one example implementation.
Figure 21:
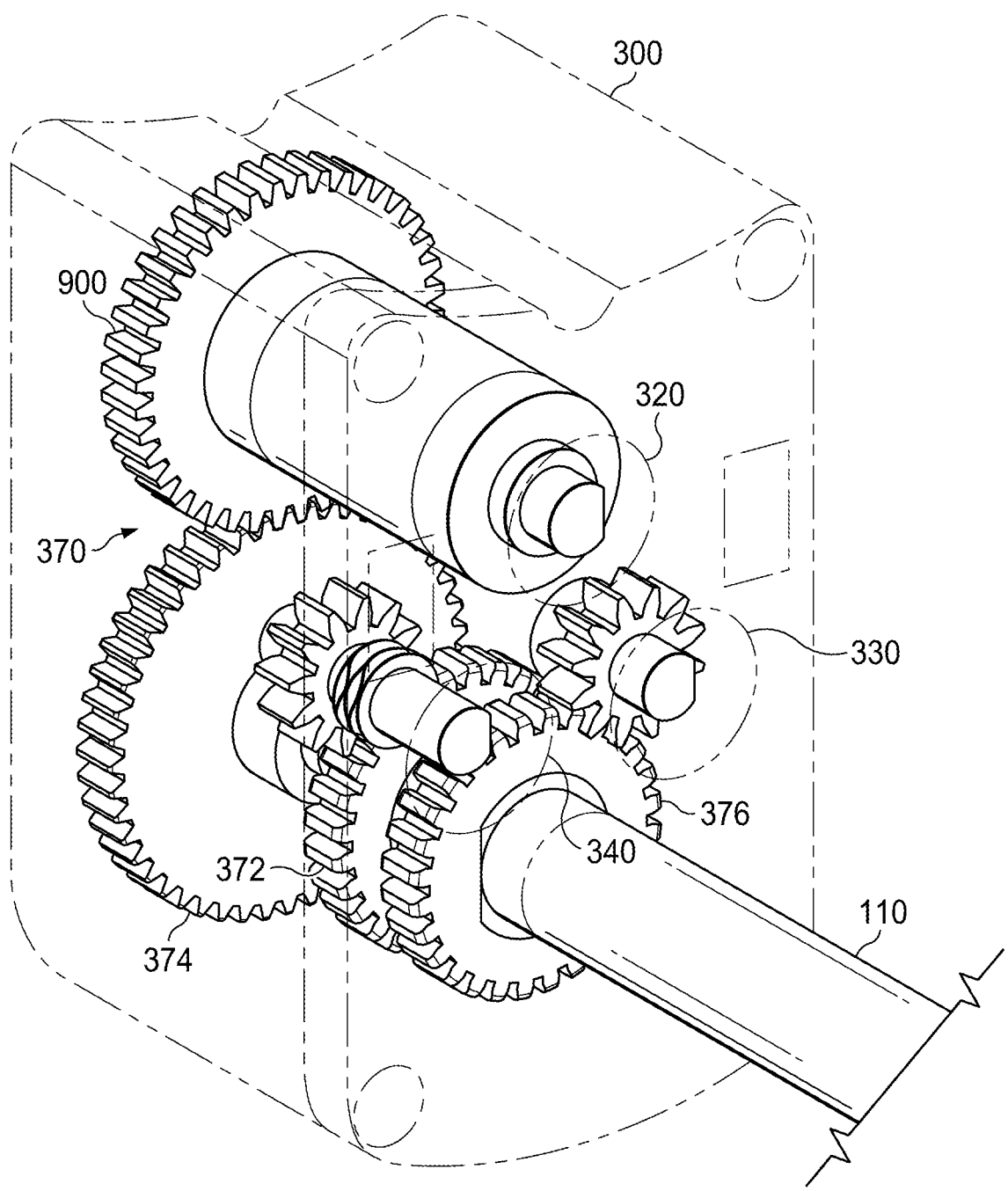
FIG. 21 depicts an example implementation of a gear assembly housed within the control housing of FIG. 20.

FIGS. 20-21 depict example gear assembly 370 housed within control housing 300. As shown in FIG. 20, each of first, second, and third rotatable platters 320, 330, 340 affects rotation of a specific mechanical feature of surgical stapling device 100. In the illustrated implementation, first rotatable platter 320 corresponds to activating firing mechanism 1100, second rotatable platter 330 corresponds to rotating elongated shaft 110, and third rotatable platter 340 corresponds to rotating drive screw 1010 to open or close anvil 220. As shown in FIG. 21, gear assembly 370 is arranged within control housing 300 to correspond to first, second, and third rotatable platters 320, 330, 340. In the illustrated implementation, closing gear 372 is arranged to correspond with third rotatable platter 340, firing gear 374 is arranged to correspond with first rotatable platter 320 (through planetary gear 900), and rotating gear 376 is arranged to correspond with second rotatable platter 330. In the illustrated implementation, closing gear 372, firing gear 374, and rotating ear 376 are axially aligned. Gear assembly 370 allows for the rotation of elongated shaft 110 and end effector 200 (through rotating gear 376), the activation of closure mechanism 1000 (through closing gear 372), and the activation of firing mechanism 1100 (through firing gear 374) to be co-radial.

Figure 22:
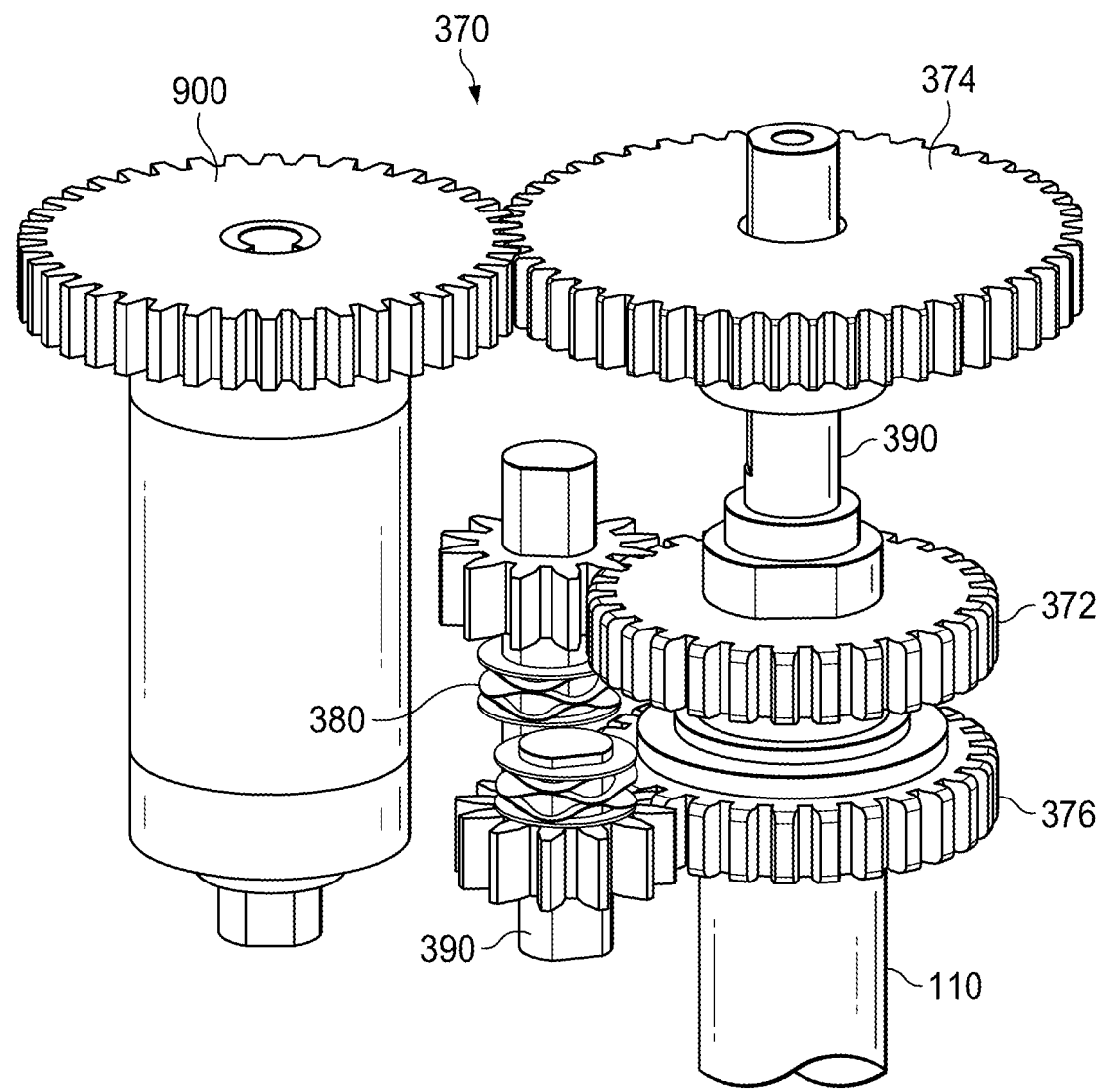
FIG. 22 depicts the gear assembly of FIG. 21, wherein springs are included on the gear shafts according to one example implementation.
Figure 23:
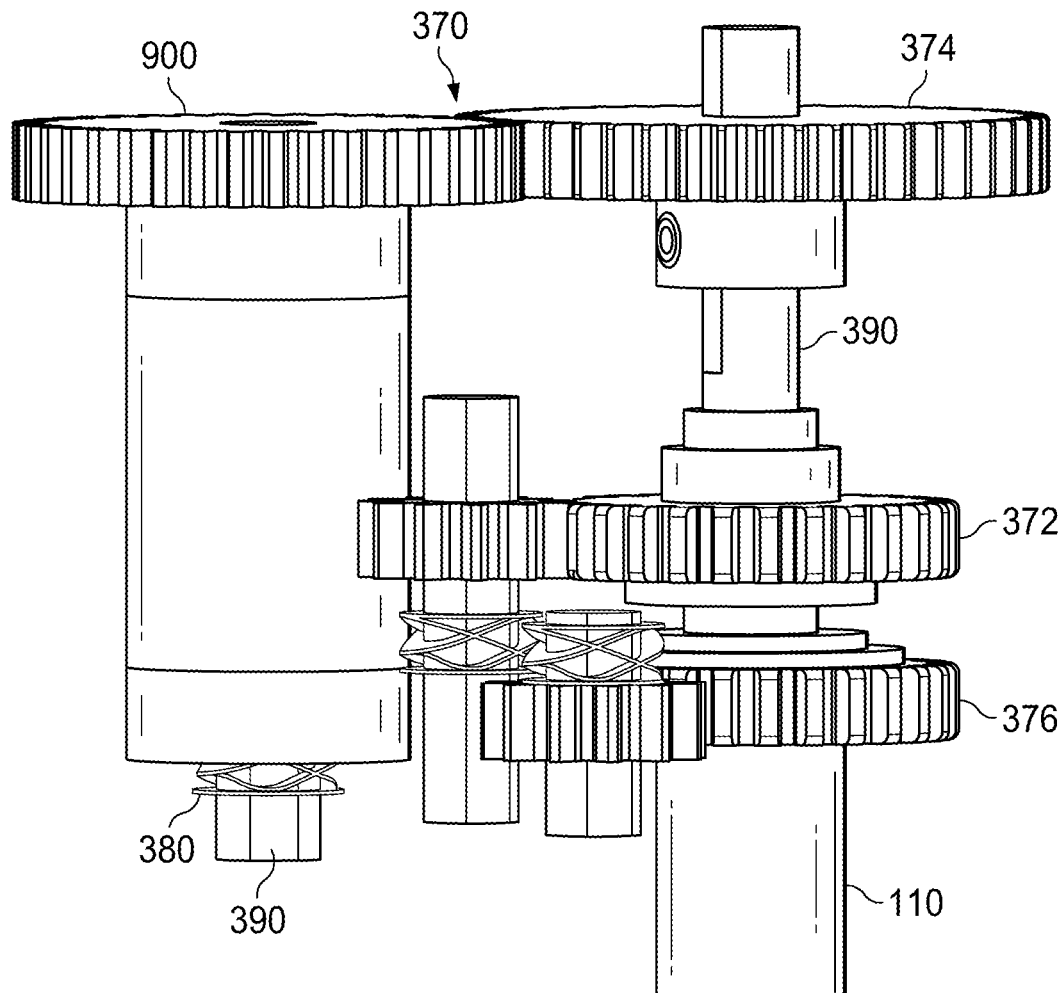
FIG. 23 is a perspective view of the gear assembly of FIG. 22.

FIGS. 22-23 depict gear assembly 370 having springs 380 on gear shafts 390, according to one example implementation As previously described, recesses 350 on first, second, and third rotatable platters 320, 330, 340 must align and accept projections 460 on first, second, and third rotatable platters 430, 440, 450 to join control housing 300 with motor housing 400. To aid in alignment of recesses 350 and projections 460, springs 380 bias first, second, and third rotatable platters 320, 330, 340 (an operational position) and allow for slight linear translation into control housing 300 (an initialization position). In some example implementations, the linear translation is approximately 0.060 inches.

With further reference to FIGS. 22-23, once first, second, and third rotatable platters 320, 330, 340 of control housing 300 are translated into the initialization position, control software of computerized surgical manipulation system 800 can rotate first, second, and third rotatable platters 320, 330, 340 of motor housing 400 to align projections 460 with recesses 350. The amount of rotation depends on the number of projections 460 and recesses 350. For example, if there are four corresponding projections 460 and recesses 350, first, second, and third rotatable platters 320, 330, 340 of motor housing 400 can be rotated clockwise and counterclockwise along a 90° arc to allow projections 460 and recesses 350 to engage. By comparison, if there are two corresponding projections 460 and recesses 350, first, second, and third rotatable platters 320, 330, 340 of motor housing 400 can be rotated clockwise and counterclockwise along a 180° arc to allow projections 460 and recesses 350 to engage. In some example implementations, initialization of first, second, and third rotatable platters 320, 330, 340 of control housing 300 is automatically executed upon detection of control housing 300 being in close proximity to motor housing 400, such as via a Hall Effect sensor or other suitable proximity sensor. Furthermore, during operation of surgical stapling device 100, various encoders associated with the motors in motor housing 400 can provide feedback for use by computerized surgical manipulation system 800 to demand the operational status of surgical stapling device 100. Due to the relatively small amount of linear translation of first, second, and third rotatable platters 320, 330, 340, closing gear 372 and rotating gear 376 remain in a meshed arrangement, even when first, second, and third rotatable platters 320, 330, 340 are in the initialization position. In some implementations, however, to achieve the desired gear reduction and torque with regard to firing mechanism 1100, planetary gearhead 900 can be used to drive firing gear 374. In accordance with such implementations, planetary gearhead 900 provides a gear reduction of approximately 104:1.

Figure 24:
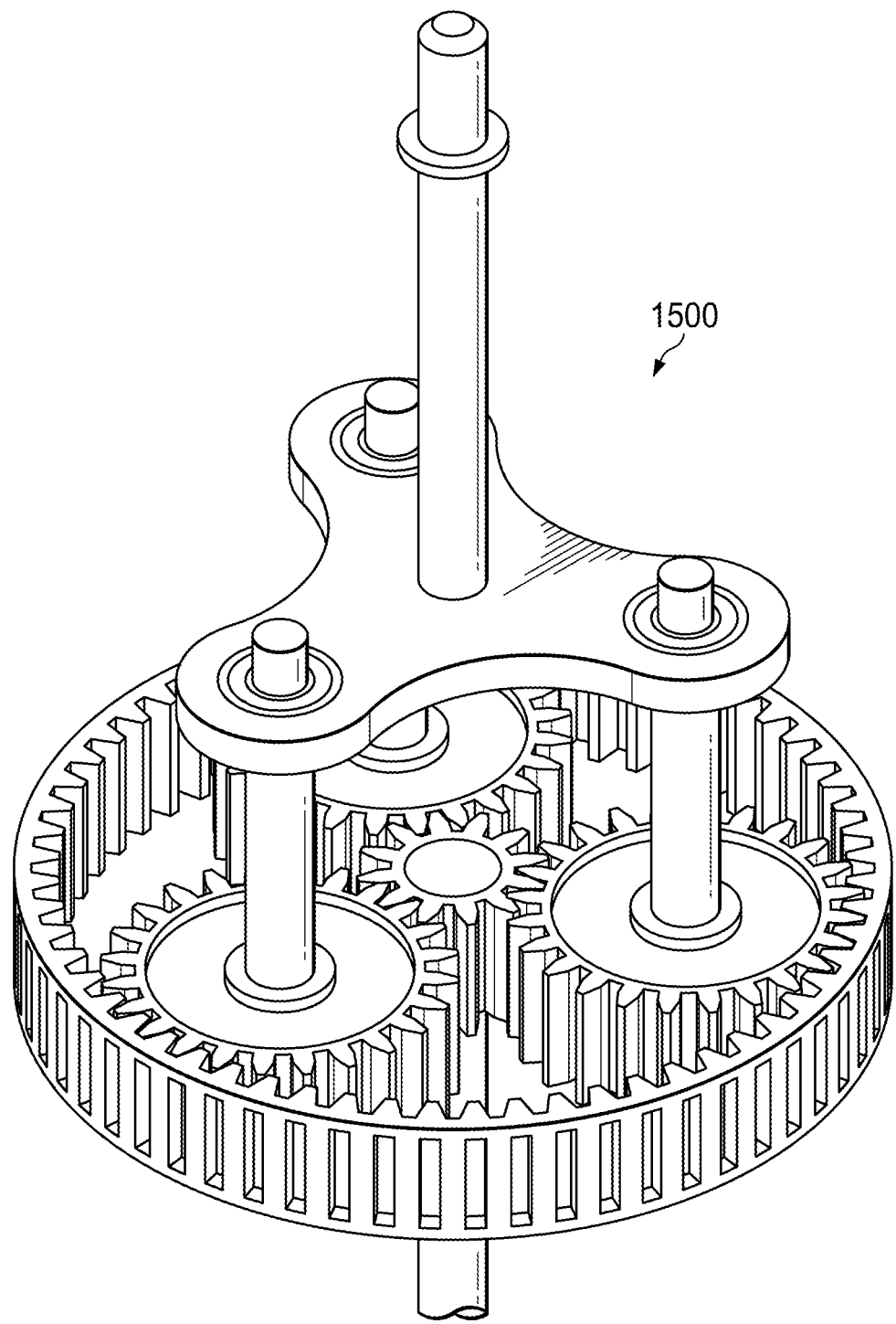
FIG. 24 depicts an example implementation of a sun gear driven by the motor housing of FIG. 4.

FIG. 24 depicts example sun gear 1500 driven by motor housing 400, which is used to drive planetary gearhead 900. When moving first rotatable platter 320 associated with firing gear 374 to its initialization position, it may be desirable to avoid re-engaging sun gear 1500 with planetary gearhead 900. As such, spring 380 can be positioned on shaft 390 external to planetary gearhead 900, and first rotatable platter 320 can ride along shaft 390. Spring 380 can bias first rotatable platter 320 into the operational position but allows first rotatable platter 320 to linearly translate along shaft 390 for initialization.

Figure 25A:
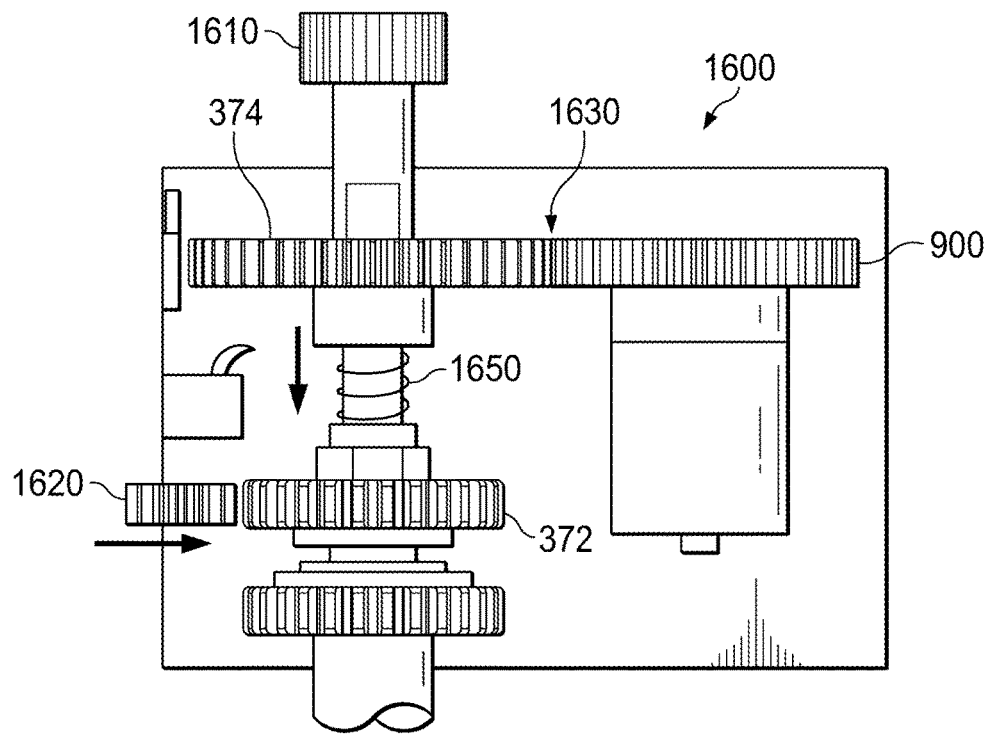
Figure 25B:
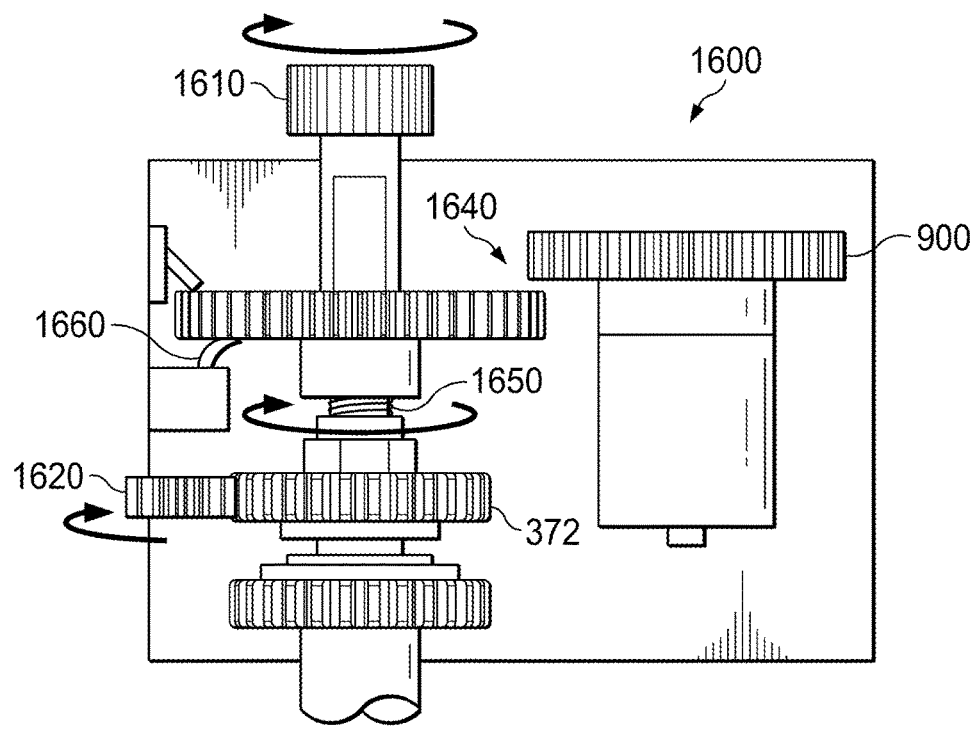

FIG. 25A-25B depicts an example implementation of bailout mechanism 1600 included in control housing 300, wherein bailout mechanism 1600 allows for manual control of various mechanical operations of surgical stapling device 100. Bailout mechanism 1600 comprises first knob 1610 for manually controlling firing gear 374 (firing mechanism 1100) and second knob 1620 for manually controlling closing gear 372 (closure mechanism 1000). In the illustrated implementation, second knob 1620 is a thumbwheel. It is to be appreciated that an additional knob can be provided for manually controlling rotating gear 376 (rotation of elongated shaft 110 and end effector 200). In the illustrated implementation, first knob 1610 is fixedly coupled to firing gear 374. During a bailout situation, a user can press first knob 1610 downward to force firing gear 374 from engaged position 1630 (shown in FIG. 25A) to disengaged position 1640 (shown in FIG. 25B). As shown in FIGS. 25A-25B, firing gear 374 can be biased towards engaged position 1630 and can be disengaged from planetary gearhead 900 by spring 1650 or other suitable biasing element. Once firing gear 374 is pushed into disengaged position 1640, pawl 1660 can be used to maintain firing gear 374 in disengaged position 1640. Further, in some implementations, a ratchet system can engage when firing gear 374 is in disengaged position 1640 to only permit rotation of firing gear 374 and first knob 1610 in a first direction (i.e., to only allow for movement of firing mechanism 1100 in reverse). As depicted in FIG. 25B, second knob 1620 can be used to selectively rotate closing gear 372 to manually open or close anvil 220 of end effector 200.

All literature and similar material cited in this application, including, but not limited to, patents, patent applications, articles, books, treatises, and web pages, regardless of the format of such literature and similar materials, are expressly incorporated by reference in their entirety. Should one or more of the incorporated references and similar materials differs from or contradicts this application, including but not limited to defined terms, term usage, described techniques, or the like, this application controls.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about", if or when used throughout this specification describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed technology. Various functions and elements described herein may be partitioned differently from those shown without departing from the scope of the disclosed technology. Generic principles defined herein may be applied to other implementations. Different numbers of a given module or unit may be employed, a different type or types of a given module or unit may be employed, a given module or unit may be added, or a given module or unit may be omitted.

Regarding this disclosure, the term "a plurality of" refers to two or more than two. Unless otherwise clearly defined, orientation or positional relations indicated by terms such as "upper" and "lower" are based on the orientation or positional relations as shown in the figures, only for facilitating description of the disclosed technology and simplifying the description, rather than indicating or implying that the referred devices or elements must be in a particular orientation or constructed or operated in the particular orientation, and therefore they should not be construed as limiting the disclosed technology. The terms "connected", "mounted", "fixed", etc. should be understood in a broad sense. For example, "connected" may be a fixed connection, a detachable connection, or an integral connection; a direct connection, or an indirect connection through an intermediate medium. For an ordinary skilled in the art, the specific meaning of the above terms in the disclosed technology may be understood according to specific circumstances.

Specific details are given in the above description to provide a thorough understanding of the disclosed technology. However, it is understood that the disclosed implementations and implementations can be practiced without these specific details. For example, circuits can be shown in block diagrams in order not to obscure the disclosed implementations in unnecessary detail. In other instances, well-known circuits, processes, algorithms, structures, and techniques can be shown without unnecessary detail in order to avoid obscuring the disclosed implementations.

The disclosed technology can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, the disclosed technology can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

It should be appreciated that all combinations of the foregoing concepts and additional concepts discussed in greater detail herein (provided such concepts are not mutually inconsistent) are contemplated as being part of the disclosed technology. In particular, all combinations of claimed subject matter appearing at the end of this disclosure are contemplated as being part of the technology disclosed herein. While the disclosed technology has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed technology in its broader aspects is not limited to any of the specific details, representative devices and methods, and/or illustrative examples shown and described. Accordingly, departures may be made from such details without departing from the spirit or scope of the general inventive concept.

What is claimed:

1. A surgical system, comprising:
    (a) a computerized surgical manipulation system having a robotic arm and a support coupled to the robotic arm;
    (b) a surgical device, wherein the surgical device includes:
        (i) an elongated shaft having a proximal end and a distal end; and
        (ii) a control housing coupled to the proximal end of the elongated shaft, wherein the control housing is configured to attach to a motor housing having a notch, wherein the motor housing is coupled to the support; and
    (c) a trocar pivotally coupled to the support such that the trocar can pivot away from axial alignment with the support,
    wherein the distal end of the elongated shaft extends into the pivoted trocar,
    wherein the trocar containing the surgical device is pivoted into axial alignment with the support such that the notch receives the elongated shaft of the surgical device,
    wherein the control housing engages the motor housing, and
    wherein the elongated shaft has a diameter portion and a reduced diameter portion, wherein the reduced diameter portion engages the notch on the motor housing.

2. The system of claim 1, wherein the surgical device further includes an end effector coupled to the distal end of the elongated shaft, wherein the end effector includes a clamping mechanism having an anvil and a cartridge for supplying surgical staples.

3. The system of claim 2, further comprising:
    (a) a closure mechanism for opening and closing the anvil on the clamping mechanism, wherein the closure mechanism is housed within the elongated shaft of the surgical device; and
    (b) a firing mechanism for activating the cartridge, wherein the firing mechanism includes:
        (i) a laminate beam having a proximate end and a distal end, wherein a blade is coupled to the distal end of the laminate beam, and wherein the proximate end of the laminate beam is placed in diversion channels within the elongated shaft of the surgical device; and
        (ii) a nut affixed to a rotating member, wherein the nut is coupled to the proximate end of the laminate beam,
    wherein the firing mechanism moves the nut from the distal end of the elongated shaft of the surgical device towards the proximal end of the elongated shaft of the surgical device; and
    wherein the laminate beam delaminates as the laminate beam moves through the diversion channels.

4. The system of claim 1, wherein the trocar includes a holding feature having an inner wall and an outer wall.

5. The system of claim 4, wherein the holding feature of the trocar is pivotally coupled to the support through a gripping member, wherein an angled gap is formed between the gripping member and the inner wall when the trocar is axially aligned with the support, and wherein a second angled gap is formed between the gripping member and the outer wall when the trocar is pivoted away from axial alignment with the support.

6. The system of claim 1, wherein the control housing has a control interface, wherein the motor housing has a motor interface, and wherein the control interface selectively attaches to the motor interface to join the control housing and the motor housing.

7. The system of claim 6, wherein the control interface and the motor interface each include a plurality of platters that are associated with specific mechanical features of the surgical device, wherein the platters on the control interface are configured to mate with the platters on the motor interface.

8. The system of claim 1, further comprising a bailout mechanism configured to the control housing for manually controlling mechanical operations of the surgical device.

9. A surgical system, comprising:
    (a) a computerized surgical manipulation system having a robotic arm and a support coupled to the robotic arm;
    (b) a surgical device, wherein the surgical device includes:
        (i) an elongated shaft having a proximal end and a distal end; and
        (ii) a control housing coupled to the proximal end of the elongated shaft, wherein the control housing is configured to attach to a motor housing having a notch, wherein the motor housing is coupled to the support; and
    (c) a trocar having a holding feature, wherein the holding feature has an inner wall and an outer wall, wherein the holding feature is pivotally coupled to the support through a gripping member such that the trocar can pivot away from axial alignment with the support,
    wherein the distal end of the elongated shaft extends into the pivoted trocar,
    wherein the trocar containing the surgical device is pivoted into axial alignment with the support such that the notch receives the elongated shaft of the surgical device,
    wherein the control housing engages the motor housing, and
    wherein an angled gap is formed between the gripping member and the inner wall when the trocar is axially aligned with the support, and wherein a second angled gap is formed between the gripping member and the outer wall when the trocar is pivoted away from axial alignment with the support.

10. The system of claim 9, wherein the surgical device further includes an end effector coupled to the distal end of the elongated shaft, wherein the end effector includes a clamping mechanism having an anvil and a cartridge for supplying surgical staples.

11. The system of claim 10, further comprising:
(a) a closure mechanism for opening and closing the anvil on the clamping mechanism, wherein the closure mechanism is housed within the elongated shaft of the surgical device; and
(b) a firing mechanism for activating the cartridge, wherein the firing mechanism includes:
  (i) a laminate beam having a proximate end and a distal end, wherein a blade is coupled to the distal end of the laminate beam, and wherein the proximate end of the laminate beam is placed in diversion channels within the elongated shaft of the surgical device; and
  (ii) a nut affixed to a rotating member, wherein the nut is coupled to the proximate end of the laminate beam,
wherein the firing mechanism moves the nut from the distal end of the elongated shaft of the surgical device towards the proximal end of the elongated shaft of the surgical device; and
wherein the laminate beam delaminates as the laminate beam moves through the diversion channels.

12. The system of claim 9, wherein the elongated shaft has a diameter portion and a reduced diameter portion, wherein the reduced diameter portion engages the notch on the motor housing.

13. The system of claim 9, further comprising a bailout mechanism configured to the control housing for manually controlling mechanical operations of the surgical device.

14. The system of claim 9, wherein the control housing has a control interface, wherein the motor housing has a motor interface, and wherein the control interface selectively attaches to the motor interface to join the control housing and the motor housing.

15. The system of claim 14, wherein the control interface and the motor interface each include a plurality of platters that are associated with specific mechanical features of the surgical device, wherein the platters on the control interface are configured to mate with the platters on the motor interface.

* * * * *